(12) United States Patent
Hanafusa et al.

(10) Patent No.: US 7,931,789 B2
(45) Date of Patent: Apr. 26, 2011

(54) DEVICE FOR CHARGING SEPARATION BUFFER LIQUID TO MICROCHIP, AND MICROCHIP PROCESSING DEVICE EQUIPPED WITH THE CHARGING DEVICE, ELECTROPHORESIS METHOD IN CAPILLARY CHANNEL AND ITS MICROCHIP PROCESSING DEVICE

(75) Inventors: Nobuhiro Hanafusa, Kyoto (JP); Tomokazu Sudo, Kyoto (JP); Katsuhiko Seki, Kyoto (JP); Koichi Suzuki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1128 days.

(21) Appl. No.: 11/493,810

(22) Filed: Jul. 27, 2006

(65) Prior Publication Data
US 2007/0175757 A1 Aug. 2, 2007

(30) Foreign Application Priority Data

Oct. 11, 2005 (JP) .................................. 2005-296459
Oct. 11, 2005 (JP) .................................. 2005-296478

(51) Int. Cl.
*G01N 27/447* (2006.01)
(52) U.S. Cl. .......................................... 204/450; 417/48

(58) Field of Classification Search .................... 417/48; 435/287.1–288.7; 422/99–100; 204/450–453, 204/600–606
See application file for complete search history.

(56) References Cited

U.S. PATENT DOCUMENTS

| 5,232,664 | A | * | 8/1993 | Krawzak et al. | ................. 422/64 |
| 6,013,168 | A | | 1/2000 | Arai | |
| 2002/0144907 | A1 | * | 10/2002 | Yamamoto | .................... 204/453 |
| 2003/0121411 | A1 | * | 7/2003 | Hoshi | ................. 92/66 |
| 2004/0018638 | A1 | | 1/2004 | Shoji et al. | |
| 2005/0161402 | A1 | | 7/2005 | Hanafusa et al. | |
| 2006/0163070 | A1 | * | 7/2006 | Boronkay et al. | ............ 204/601 |

* cited by examiner

*Primary Examiner* — Ula C Ruddock
*Assistant Examiner* — Gurpreet Kaur
(74) *Attorney, Agent, or Firm* — Manabu Kanesaka

(57) ABSTRACT

In a separation buffer solution filling device, a microchip is arranged such reservoirs are opened on a surface on respective ends of channels including at least a main separation channel in which analysis is performed while a solution moves inside a plate-like member, and the reservoirs face upward. The filling device fills separation buffer solution into the channels by supplying air from an air supply port which is pushed while maintaining air-tightness onto a top of the reservoir filled with the separation buffer solution on either end of said channels. The air supply port is an opening on a front end of an air cylinder, and has a seal part on that opening. The filling device is pushed onto the reservoir while maintaining air-tightness by that seal part.

9 Claims, 20 Drawing Sheets

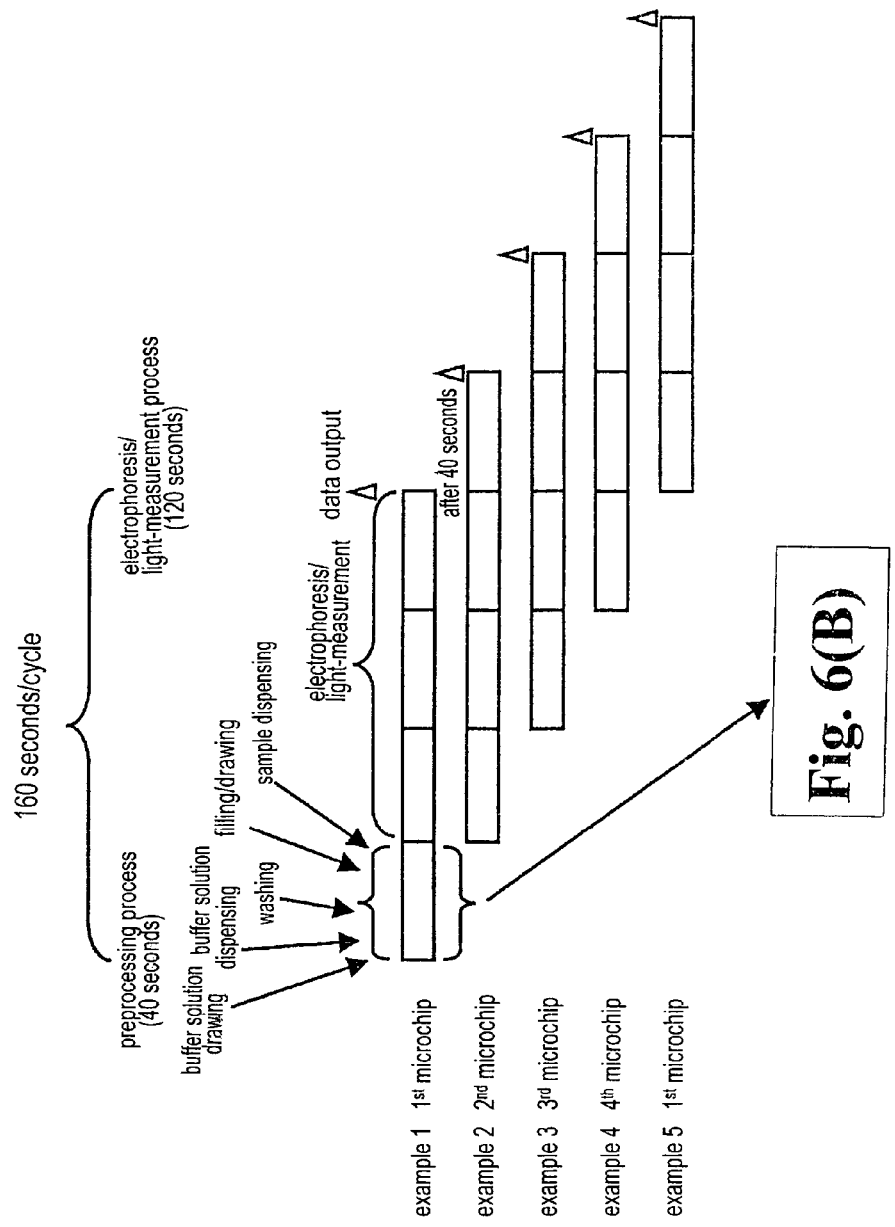

Fig. 8

[remaining liquid quantity display]

gel

| | remaining liquid quantity (μL) | required liquid quantity (μL) |
|---|---|---|
| DNA—A | 2100 | 3000 |
| DNA—B | 1300 | 3000 |
| DNA—C | 1050 | 3000 | marker

| | remaining liquid quantity (μL) | required liquid quantity (μL) |
|---|---|---|
| DNA—A | 200 | 450 |
| DNA—B | 210 | 450 |
| DNA—C | 180 | 450 |

[request form]

| No | container No | name of sample | measurement item | memo |
|---|---|---|---|---|
| 1 | A1 | XXXXX01 | DNA—B | |
| 2 | A2 | XXXXX02 | DNA—B | |
| 3 | A3 | XXXXX03 | DNA—C | |

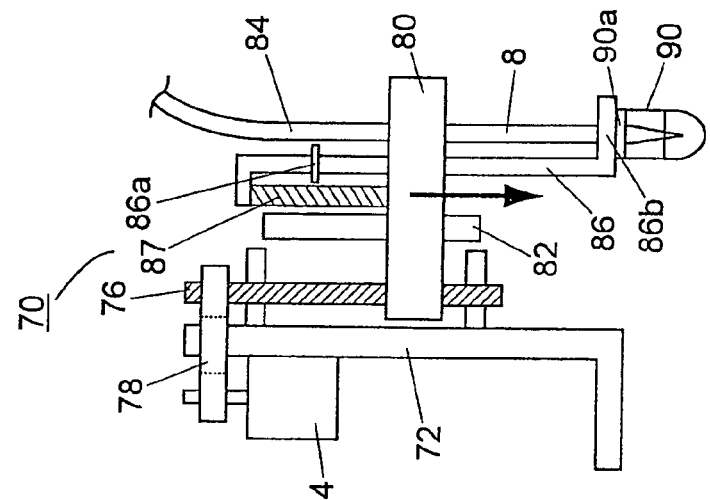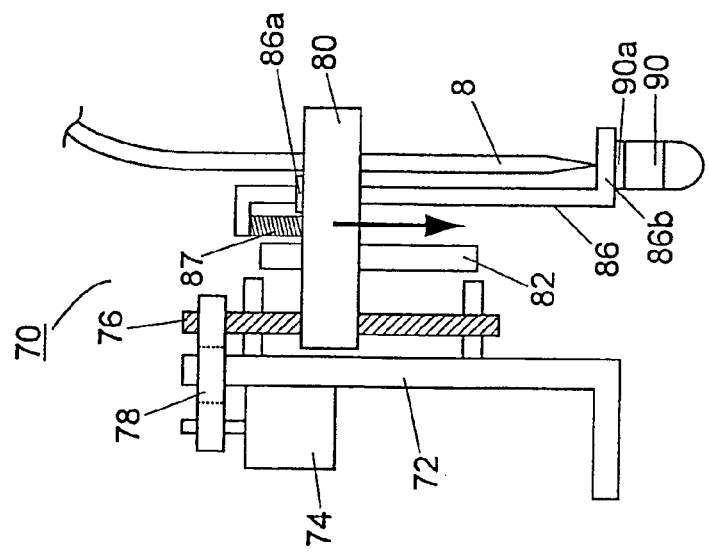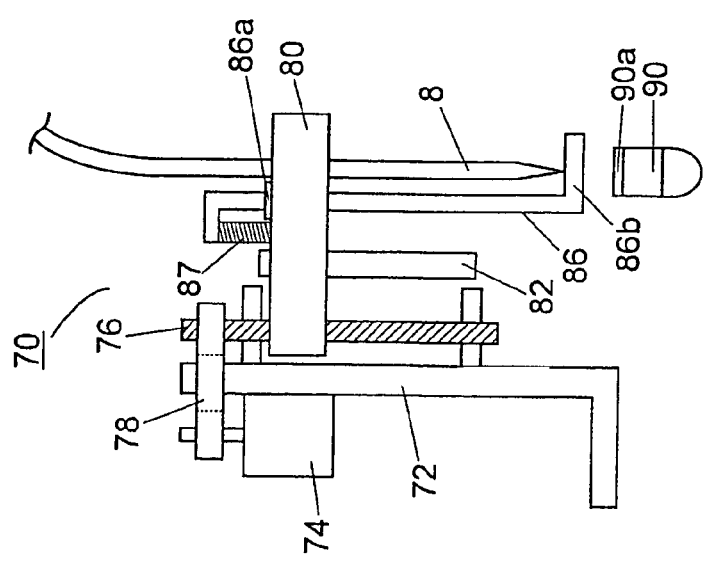

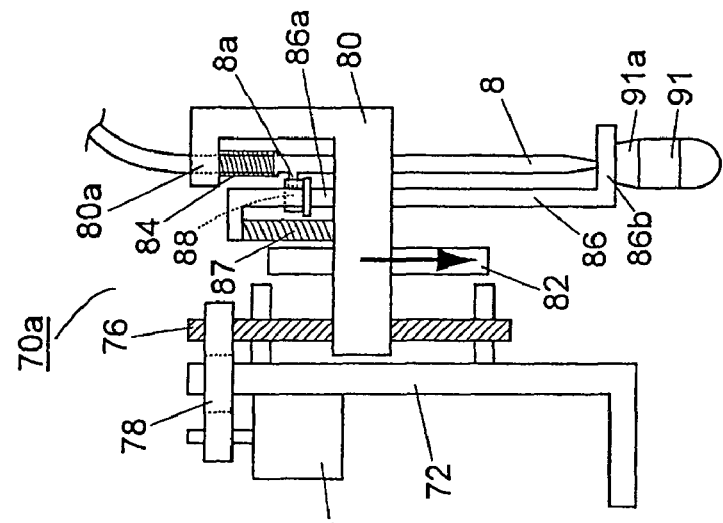
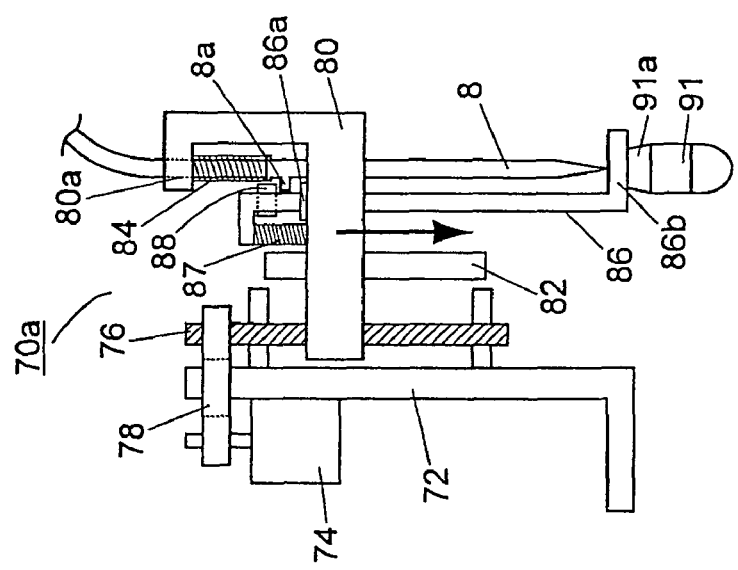
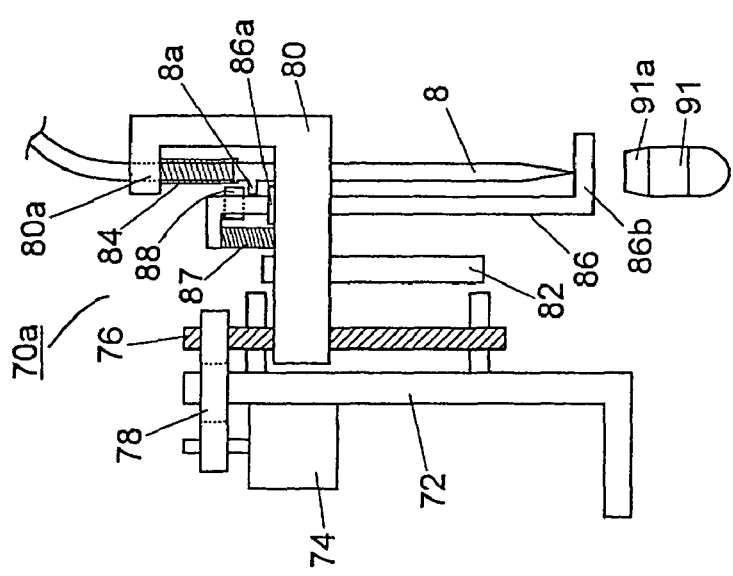

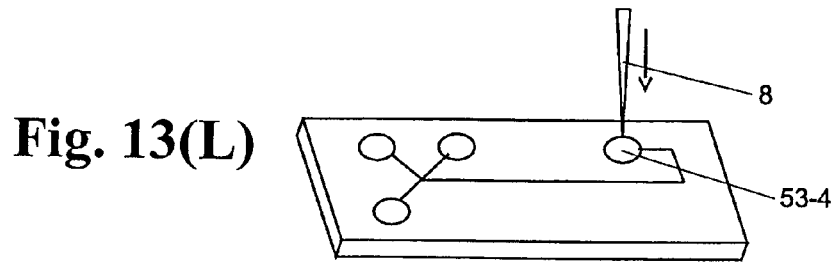
Fig. 13(L)
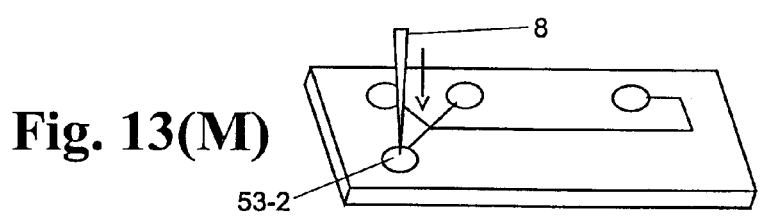
Fig. 13(M)
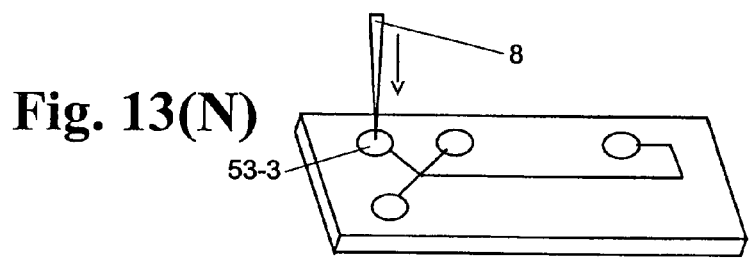
Fig. 13(N)
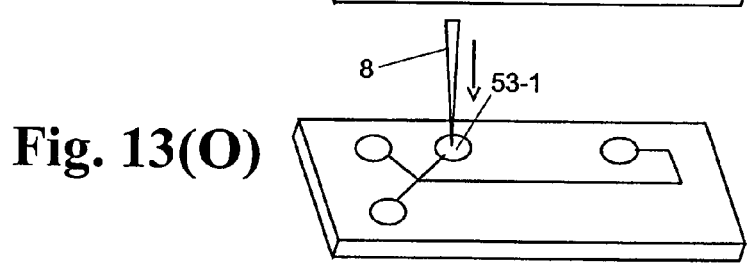
Fig. 13(O)
Fig. 13(P)
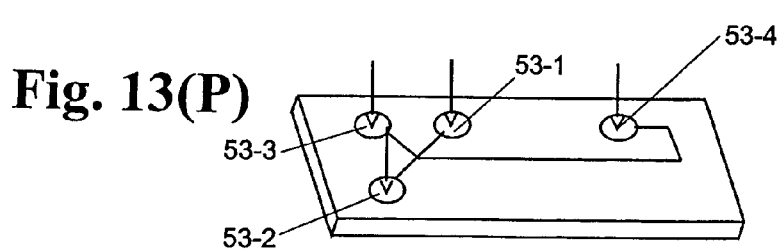 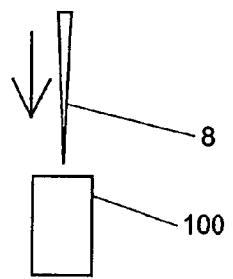
Fig. 13(Q)
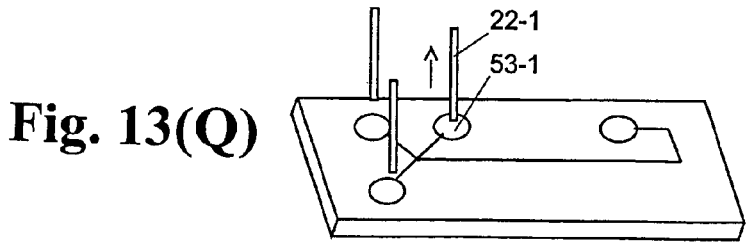 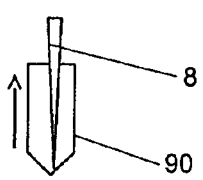

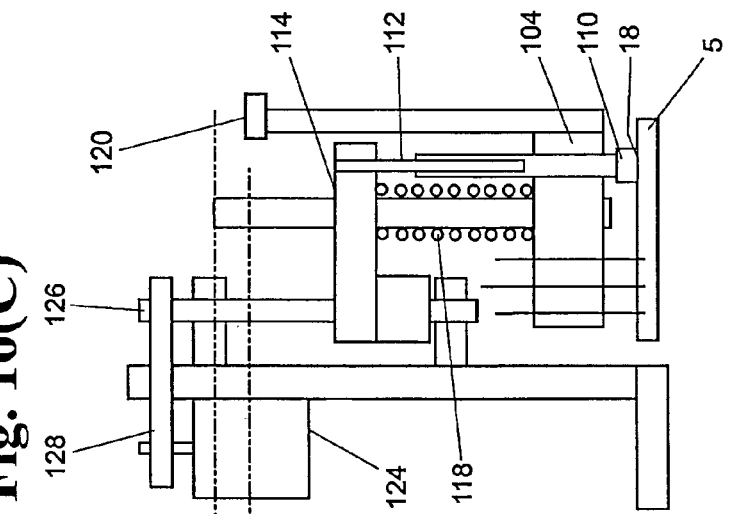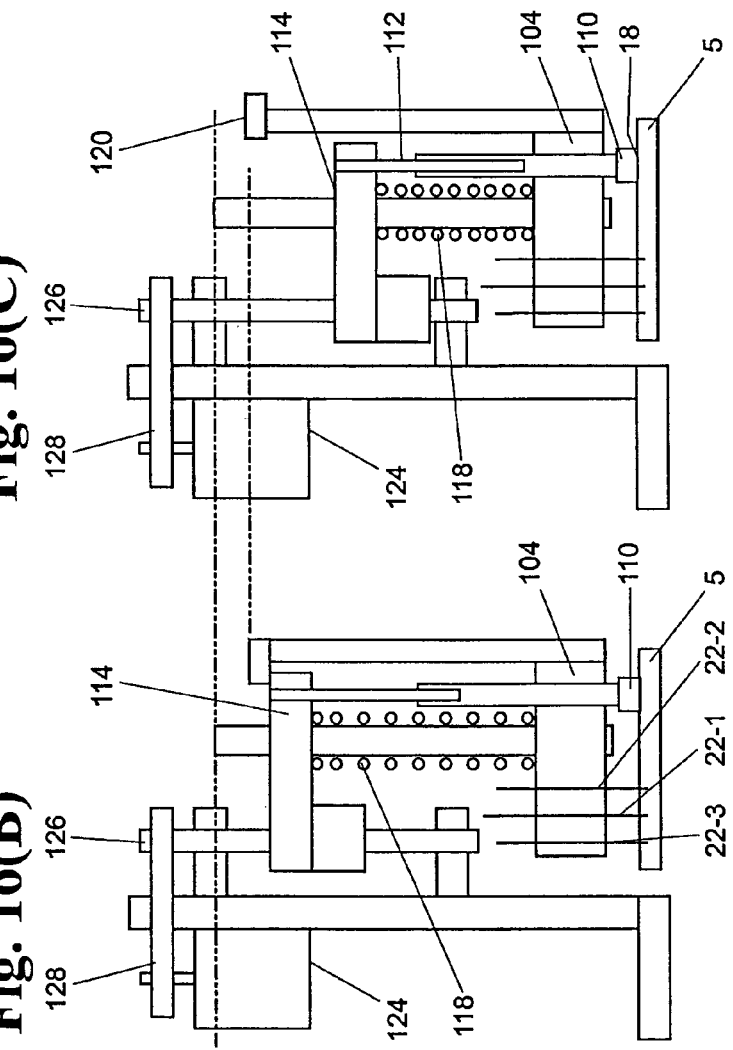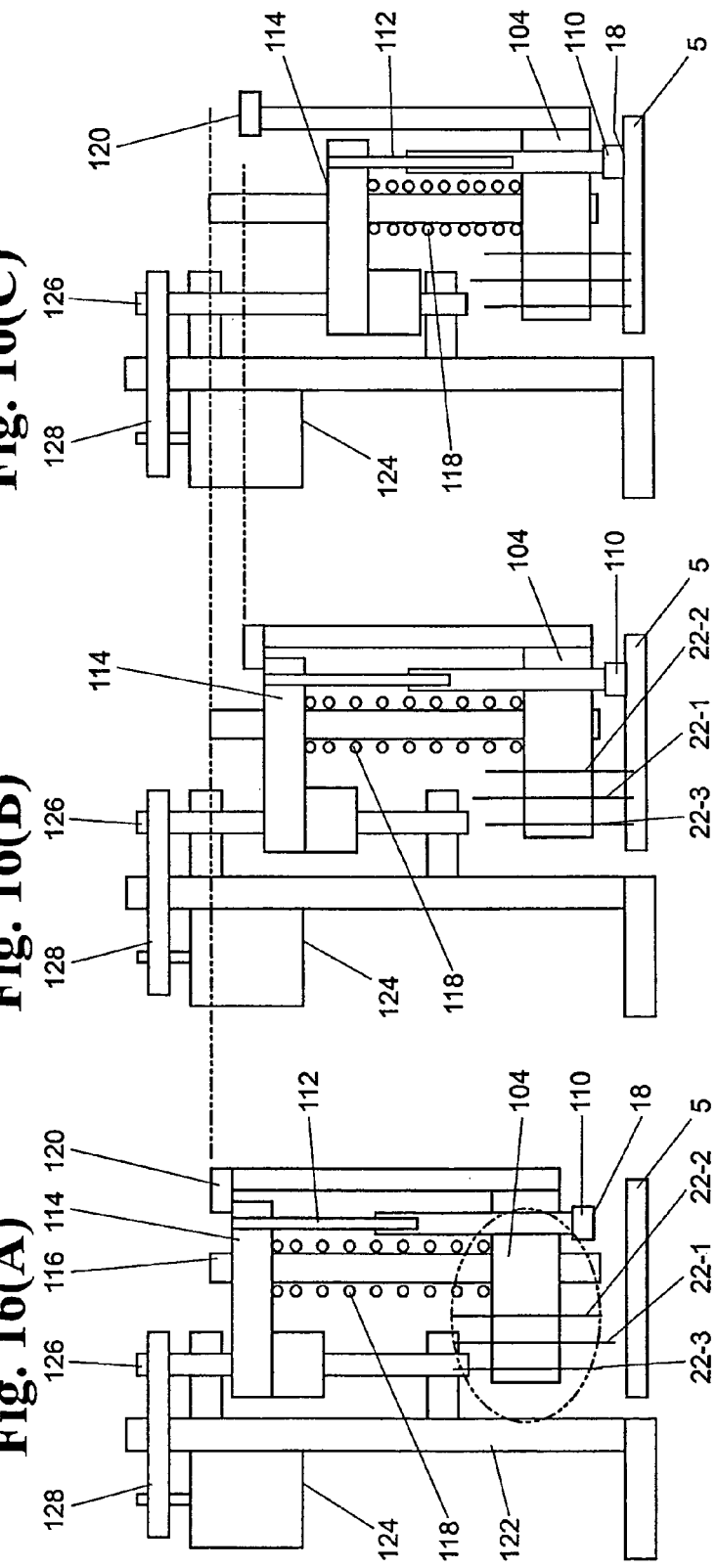

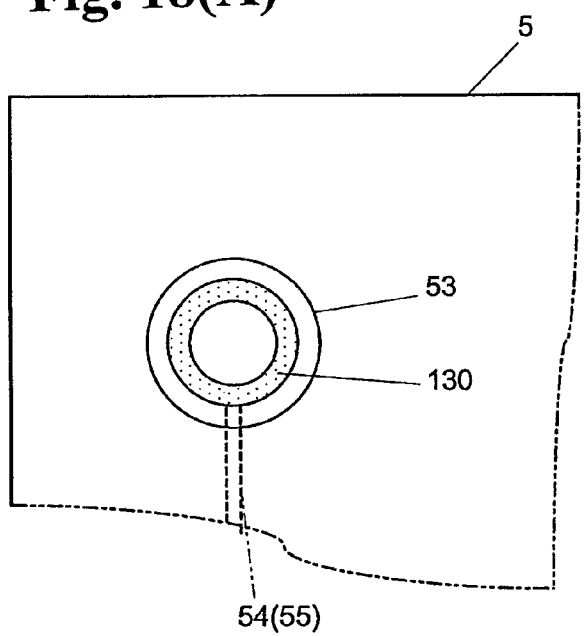
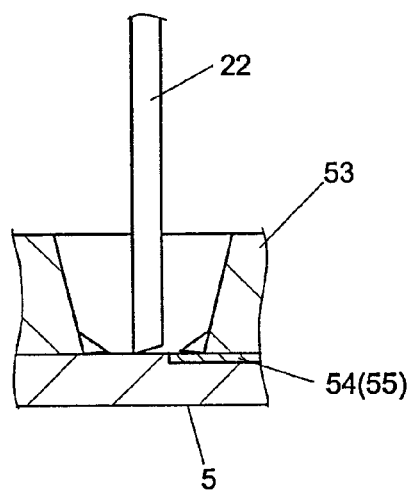
Fig. 18(A)
Fig. 18(B)

DEVICE FOR CHARGING SEPARATION BUFFER LIQUID TO MICROCHIP, AND MICROCHIP PROCESSING DEVICE EQUIPPED WITH THE CHARGING DEVICE, ELECTROPHORESIS METHOD IN CAPILLARY CHANNEL AND ITS MICROCHIP PROCESSING DEVICE

BACKGROUND OF THE INVENTION AND RELATED ART STATEMENT

The present invention relates to a microchip processing apparatus for performing analysis by a microchip electrophoresis method or micro liquid chromatography, or the like, in fields such as chemistry and life science, and a device for filling separation buffer solution into a microchip in such a microchip processing apparatus. Also, the present invention relates to a capillary electrophoresis method for separating and analyzing samples, and a microchip processing apparatus for realizing such a capillary electrophoresis method.

In microchip electrophoresis, a sample such as DNA, RNA or protein introduced on one side of a main separation channel, is electrophoretically separated toward the other end of that channel by a voltage applied between both ends of that channel.

In microchip electrophoresis, an apparatus that automatically performs filling of buffer solution, dispensing of samples, electrophoresis, and detection of separated sample components by repeatedly using a single microchip having one electrophoresis channel has been developed (see Patent Document 1).

Electrophoresis apparatus having plural channels in order to raise operating efficiency of analysis also have been proposed. One of these apparatus has 12 channels, and after manually filling of the separation buffer solution and dispensing of the samples, it electrophoretically separates them sequentially from the 12 channels and obtains data (see Non-Patent Document 1).

Another device has 12 channels using capillaries, and it is made so as to automatically perform: filling of separation buffer solution, dispensing of samples, electrophoretic separation, and data acquisition (see Non-Patent Document 2).

In micro liquid chromatography, the microchip has a liquid delivery channel including a separation column in the form of a main channel, and separates and analyzes a sample introduced to one side of the separation column by moving it toward the other end of that separation column (see Non-Patent Document 3).

Patent Document 1: Publication of Japanese Unexamined Patent No. H10-246721
Non-Patent Document 1: "Bunseki" ("Analytical Sciences"), No. 5, pp. 267-270 (2002)
Non-Patent Document 2: Electrophoresis 2003, 24, 93-95
Non-Patent Document 3: Anal. Chem., 70, 3790 (1998)

A microchip having reservoirs opened on the surface on the respective ends of the channels is used, and the microchip is held in a manner such that the reservoirs face upward when installing on the microchip processing apparatus. At that time, when filling separation buffer solution into the channels, or when exchanging the separation buffer solution of the channels of the microchip having finished analysis, the separation buffer solution is supplied to one reservoir by a separation buffer solution filling device. The separation buffer solution is pushed into the channels by pushing an air supply port onto that reservoir and supplying air, and the separation buffer solution overflowing from the other reservoirs, is drawn off by a suction nozzle.

At this time, because it is common that the mechanism for pushing the air supply port onto the reservoir and the driving mechanism for supplying air are separate mechanisms, the apparatus tends to become bulky. Also, it is not good that the separation buffer solution which is supposed to be drawn from the reservoirs by the suction nozzle and discharged, remains in the reservoirs, and in particular when, due to repeated used of the microchip, contamination from the analytical sample of the previous time occurs and the analytical precision is lowered.

Also, in capillary electrophoresis, after the separation buffer solution is filled into the channels and the sample is injected into the channels, it is determined as to whether the phoresis operation is being performed normally or whether it will be performed normally. The method for that is a method in which the electrical current value in the sample phoresis is compared with a threshold value after starting electrophoresis of the sample, or a test current value by application of a voltage lower than the electrophoresis voltage is compared with a threshold value. In either case the normality or abnormality of phoresis is determined according to the electrified state after sample introduction. Further, the electrophoresis process is discontinued when it is determined not to be normal.

However, with the method that determines whether phoresis is normal or not after injecting the sample into the channels, because the sample submitted to analysis is already lost when it is determined not to be normal, it is difficult to measure it again in the case of a sample that can be obtained only in a small quantity.

Therefore, the first purpose of the present invention is to provide a compact and inexpensive separation buffer solution filling device by simplifying the mechanism for pushing the air supply port onto the reservoir and supplying air.

The second purpose of the present invention is to provide a separation buffer solution filling device that makes it easier to draw the separation buffer solution to be discharged from the reservoirs when filling the separation buffer solution into the channels of the microchip.

The third purpose of the present invention is to provide a microchip processing apparatus using such a separation buffer solution filling device.

The fourth purpose of the present invention is to make it such that it can be determined as to whether the filling of the separation buffer solution into the channels has been performed normally even without introducing the sample into the channels.

SUMMARY OF THE INVENTION

The separation buffer solution filling device of the present invention for achieving the first purpose, is a separation buffer solution filling device for a microchip having reservoirs opened on the surface on the respective ends of channels including at least a main separation channel in which analysis is performed while a solution moves inside a plate-like member which is placed in a manner such that the reservoirs face upward, for filling separation buffer solution into the channels by supplying air from an air supply port which is pushed while maintaining air-tightness onto the top of a reservoir filled with separation buffer solution on either end of the channels.

This air supply port is an opening on the front end of an air cylinder, and has a seal part on that opening which is pushed onto the reservoir to maintain an air-tightness. An air cylinder moving/driving mechanism for moving the air cylinder in the vertical direction and operating a plunger thereof, comprises an air cylinder holding member for holding the air cylinder, a plunger holding member for holding the plunger above the air cylinder holding member, a guide for supporting the air cylinder holding member and plunger holding member so as to be capable of sliding, an elastic member placed between the air cylinder holding member and plunger holding member, a driving mechanism for moving the plunger holding member in the vertical direction, and a stopper for defining a top dead center of the plunger holding member. The elastic member is set in a manner such that, in the process of the descent of the plunger holding member accompanying the operation of the driving mechanism, the air cylinder holding member is pushed downward by the elastic member until the air supply port contacts the microchip, and the plunger is pushed to supply air from the air supply port after the air supply port contacts with the microchip.

The separation buffer solution filling device of the present invention for achieving the second purpose, is for a microchip having reservoirs opened on the surface on the respective ends of channels including at least a main separation channel in which analysis is performed while a solution moves inside a plate-like member which is placed in a manner such that the reservoirs face upward, for filling separation buffer solution into the channels. This device has an air supply port which is pushed while maintaining air-tightness, onto the top of a reservoir filled with separation buffer solution, on either end of a channel of the microchip. Suction nozzles which are inserted from above into all of the remaining other reservoirs and draw separation buffer solution overflowing into the reservoirs from the channels when separation buffer solution is pushed into the channels by air being blown from the air supply port. These suction nozzles are supported so as to be capable of sliding via a nozzle holding member which moves in the vertical direction, and are forced downward by a forcing means, whereby they assume a state, forced by the forcing means, wherein they are pushed against the bottoms of the reservoirs.

Of the reservoirs, the reservoir for sample supply may have the separation buffer solution removed or be washed. In order to respond to such a situation, in a preferred embodiment, it is attached in a manner such that, in the state before the suction nozzles are inserted into the reservoirs, the length by which the suction nozzle inserted into the sample supply reservoir among the suction nozzles, projects downward from the nozzle holding member, compared with the length by which the other suction nozzles project downward from the nozzle holding member, is longer than the amount of depth of the liquid present in the reservoirs into which the other suction nozzles are inserted.

In a more preferred embodiment, the outer diameter of the front end of the suction nozzle is smaller than the size of the bottom of the reservoir into which it is inserted, and it is made such that the front end of the suction nozzle is pushed against a side wall part on the bottom of the reservoir when the suction nozzle imbibes liquid from the reservoir.

In a more preferred embodiment, the air supply port is an opening on the front end of an air cylinder, and has a seal part on that opening so that it can be pushed onto the reservoir while maintaining air-tightness by that seal part.

In a more preferred embodiment, an air cylinder moving/driving mechanism for moving the air cylinder in the vertical direction and operating a plunger thereof comprises an air cylinder holding member for holding the air cylinder, a plunger holding member for holding the plunger above the air cylinder holding member, a guide for supporting the air cylinder holding member and plunger holding member to be capable of sliding, an elastic member placed between the air cylinder holding member and plunger holding member, a driving mechanism for moving the plunger holding member in the vertical direction, and a stopper for defining a top dead center of the plunger holding member. The elastic member is set in a manner such that in the process of descending of the plunger holding member accompanying operation of the driving mechanism, the air cylinder holding member is pushed downward by the elastic member until the air supply port contacts the microchip, and the plunger is pushed to supply air from the air supply port after the air supply port contacts with the microchip.

In a more preferred embodiment, the air cylinder holding member is integrated with the nozzle holding member.

The microchip processing apparatus to which the present invention is applied is not limited in particular. However, a preferred example is a microchip processing apparatus, comprising at least a holding part for holding a microchip having at least a main separation channel in which analysis is performed while a solution moves inside a plate-like member, a separation buffer solution filling device for filling separation buffer solution into a channel of the microchip, a dispensing probe which is inserted from above into a sample container or a reagent container for imbibing a sample or a reagent and injecting it to a prescribed position on a microchip held on the holding part, and a dispensing probe driving mechanism for moving the dispensing probe between prescribed positions of the microchip, sample container, and reagent container. A separation buffer solution filling device of the present invention is used as that separation buffer solution filling device.

In a preferred example of such a microchip processing apparatus, the holding part holds a microchip in a manner such that the number of main channels becomes plural, a control part is provided in order to control a preprocessing process and an analysis process in the main channels, and the dispensing probe is used commonly by the plural main channels, and performs the preprocessing process in advance of the analysis process in those main channels. This control part controls so that the preprocessing process is performed independently for each main channel such that it moves to the preprocessing process of the next main channel when the preprocessing process in one main channel is finished, and the analysis process is performed in parallel in plural main channels having finished the preprocessing process.

The electrophoresis method of the present invention for achieving the fourth purpose is an electrophoresis method, in which a separation buffer solution is filled into a capillary channel and then a sample is injected and the sample components are electrophoretically separated from one end toward the other end of the capillary channel, and includes a process in which, after filling separation buffer solution into the capillary channel and before injecting the sample, a voltage is applied to the capillary channel to determine whether the filling of the separation buffer solution is normal or not from the electrified state at that time.

One example of a capillary channel is one that is formed inside a plate-like member constituting a microchip, and that microchip has reservoirs opened on the surface of the plate-like member on the respective ends of the capillary channel. In this case, this electrophoresis method injects a sample into one reservoir after filling the separation buffer solution into the capillary channel.

The microchip processing apparatus to which the electrophoresis method of the present invention for achieving the fourth purpose is applied, is not specifically limited, and for example, it can take the form of a microchip processing apparatus, comprising a holding part for holding a microchip having channels including a main separation channel in which analysis is performed while a solution moves inside a plate-like member, a separation buffer solution filling device for filling separation buffer solution into the microchip, a sample injection device for injecting a sample into the microchip, a power supply device for applying electrophoresis voltage to the main channel, and a control part for controlling filling of separation buffer solution into the channel, introduction of samples, and electrophoretic separation. In this case, it is arranged that the control part also includes a function by which, after filling separation buffer solution into the channel and before injecting the sample into the channel, a voltage is applied to the channel by the power supply device and the electrified state at that time is monitored, and it is determined from that electrified state as to whether the filling of the buffer solution is normal or not.

As for the case when the filling of the separation buffer solution is not normal, mixing of dirt and bubbles into the separation buffer solution can be mentioned. When such foreign matter is mixed in and a voltage is applied to the channel, the electrical current value expected from that applied voltage value does not occur. Therefore, it can be determined as to whether the filling of the separation buffer solution is normal or not even before introduction of the sample to the channel.

One embodiment of the electrified state used for determining the state of filling of the separation buffer solution is the size of the electrical current value. In that case, it is determined to be normal when a current value in a predetermined range flows when a predetermined voltage is applied.

The voltage value applied to the channel for determining the electrified state may be the phoresis voltage for performing electrophoresis to analyze samples, but it also may be set to a value different from the phoresis voltage. Also, it can be arranged such that refilling of separation buffer solution is performed when the filling of the separation buffer solution is not judged to be normal according to the electrified state.

In a preferred example of the electrophoresis method of the present invention, the capillary channels are prepared in a manner such that there are plural capillary channels serving as main separation channels in which samples are analyzed while moving, and a common separation buffer solution filling device and a common sample injection device are prepared for the capillary channels including those plural main channels. An electrophoresis power supply device is prepared for each main channel, and when the separation buffer solution filling process concerning one main channel is finished, a voltage is applied in the capillary channels including the main channel to determine whether the filling of the separation buffer solution is normal or not from the electrified state at that time. If it is normal, a sample is injected into the capillary channels including the main channel, and then the process moves to the separation buffer solution filling process of the capillary channels including the next main channel. In such manner the process from filling of separation buffer solution to sample injection is performed sequentially for each main channel, and the process of analysis by electrophoresis after sample injection is performed independently while partially overlapping in plural main channels.

In a preferred example of the microchip processing apparatus of the present invention, the holding part places the microchip in a manner such that the number of main channels becomes plural, the separation buffer solution filling device and sample injection device are common to the channels including those plural main channels, a power supply device is provided for each main channel, and the control part controls as follows. When the separation buffer solution filling process concerning one main channel is finished, a voltage is applied in the channels including that main channel to determine whether the filling of the separation buffer solution is normal or not from the electrified state at that time. If it is normal, a sample is injected into the channels including that main channel, and then it moves to the separation buffer solution filling process of the channels including the next main channel. In such manner the process from filling of separation buffer solution to sample injection is performed sequentially for each main channel, and the process of analysis by electrophoresis after sample injection is performed independently while partially overlapping in plural main channels.

In the separation buffer solution filling device, if the air supply port for supplying air to push the separation buffer solution into the channels is made as a hole on the front end of the air cylinder, there is no need to separately provide an air supply means so the device becomes compact.

Also, as an air cylinder moving/driving mechanism for moving that air cylinder in the vertical direction and operating the plunger thereof, the air cylinder holding member and plunger holding member are supported to be capable of sliding by a guide, and an elastic member is placed between the air cylinder holding member and plunger holding member. If it is made such that the air cylinder holding member is pushed downward by the elastic member until the air supply port contacts with the microchip, and the plunger is pushed to supply air from the air supply port after the air supply port contacts with the microchip, the movement of the air cylinder in the vertical direction and the driving of the plunger can be realized with one driving source. Therefore, the air cylinder moving/driving mechanism becomes simple, and the separation buffer solution filling device becomes compact and inexpensive.

Also, in the separation buffer solution filling device, if it is made such that the suction nozzles which are pushed into the channels and draw separation buffer solution overflowing from the other reservoirs are supported to be capable of sliding by a nozzle holding member which moves in the vertical direction, and they are forced downward by a forcing means to be pushed against the bottoms of the reservoirs, it becomes possible to draw the separation buffer solution to be discharged from the reservoir without leaving any.

The length by which the suction nozzle inserted into the sample supply reservoir among the suction nozzles projects downward from the nozzle holding member, compared with the length by which the other suction nozzles project downward from the nozzle holding member, is made longer than the amount of depth of the liquid present in the reservoirs into which those other suction nozzles are inserted. By this, because it becomes possible to draw only the liquid of the sample supply reservoir, it becomes possible to remove the separation buffer solution or perform washing of only the sample supply reservoir.

If it is made such that the front end of the suction nozzle is pushed against a side wall part on the bottom of the reservoir when imbibing liquid from the reservoir, it becomes possible to draw up to the liquid remaining at the peripheral part of the bottom of the reservoir. As a result, in the case when repeatedly using the microchip, there is less contamination (carryover) from the sample measured the previous time. Also, it becomes sufficient with less quantity of wash liquid when washing the reservoirs, and the washing time can be shortened, and consequently it is connected to shortening of the analysis time.

If the air cylinder holding member and the nozzle holding member are integrated, the separation buffer solution filling device becomes even more compact and inexpensive. Also, if a separation buffer solution filling device of the present invention is mounted on the microchip processing apparatus, it becomes easier to discharge superfluous separation buffer solution and wash liquid from the reservoirs so the analytical precision can be increased.

In the electrophoresis method and microchip processing apparatus of the present invention, because a voltage is applied to the capillary channel to determine whether the filling of the separation buffer solution is normal from the electrified state at that time after filling the separation buffer solution into the capillary channel and before injecting the sample, even if it was determined that the filling of the separation buffer solution is not normal, there is no loss of sample because the sample has not been injected at that time.

If it is made so as to determine whether the filling of the separation buffer solution is normal or not according to the size of the electrical current value, the determination can be performed by a simple means. If the voltage for determining the electrified state is set greater than the phoresis voltage, the electrified state can be determined with high sensitivity. Conversely, if the voltage for determining the electrified state is set smaller than the phoresis voltage, even if there were bubbles, it is possible to prevent damage to the capillary due to concentration of electrical field in the bubble part.

If the voltage applied to the channel for determining the electrified state is made smaller than the phoresis voltage, it is possible to control the power consumption. Also, if it is made such that refilling of separation buffer solution is performed when it is not judged that the filling of the separation buffer solution is normal, it is not necessary to perform a worthless electrophoresis process, and the operating efficiency is improved.

BRIEF DESCRIPTION OF THE DRAWINGS

FIGS. 3(A) and 3(B) are plan views showing the transparent plate-like members constituting the microchip, and FIG. 3(C) is a front view of the microchip.

FIG. 6(A)-6(B) are time charts showing the operation of the same microchip electrophoresis apparatus.

FIG. 8 is a drawing showing one example of a display screen for displaying the remaining liquid quantity in the reagent container.

FIG. 9(A)-FIG. 9(C) are front views showing the dispensing probe driving mechanism in one working example; FIG. 9(A) shows the waiting position, FIG. 9(B) shows the process of descending for sample imbibing, and FIG. 9(C) shows the sample imbibing position.

FIG. 10(A)-FIG. 10(C) are front views showing the dispensing probe driving mechanism in another working example; FIG. 10(A) shows the waiting position, FIG. 10(B) shows the process of descending for sample imbibing, and FIG. 9(C) shows the state when having sensed contact with foreign matter.

FIG. 12(F)-FIG. 12(K) are perspective views showing the operation of the same working example in the order of processes after that.

FIG. 13(L)-FIG. 13(Q) are perspective views showing the operation of the same working example in the order of processes further after that.

FIG. 14(R)-FIG. 14(U) are perspective views showing the operation of the same working example in the order of processes further after that.

FIG. 16(A)-FIG. 16(C) are front views showing the separation buffer solution filling device in one working example; FIG. 16(A) shows the waiting state, FIG. 16(B) shows the state when the air supply port and the suction nozzle are pushed against the microchip, and FIG. 16(C) shows the process of pressing separation buffer solution into the channel.

FIG. 18(A) and FIG. 18(B) are drawings showing the state of drawing liquid from the reservoir by the suction nozzle; FIG. 18(A) is a plan view, and FIG. 18(B) is a sectional view.

DETAILED DESCRIPTION OF PREFERRED EMBODIMENTS

Figure 1:
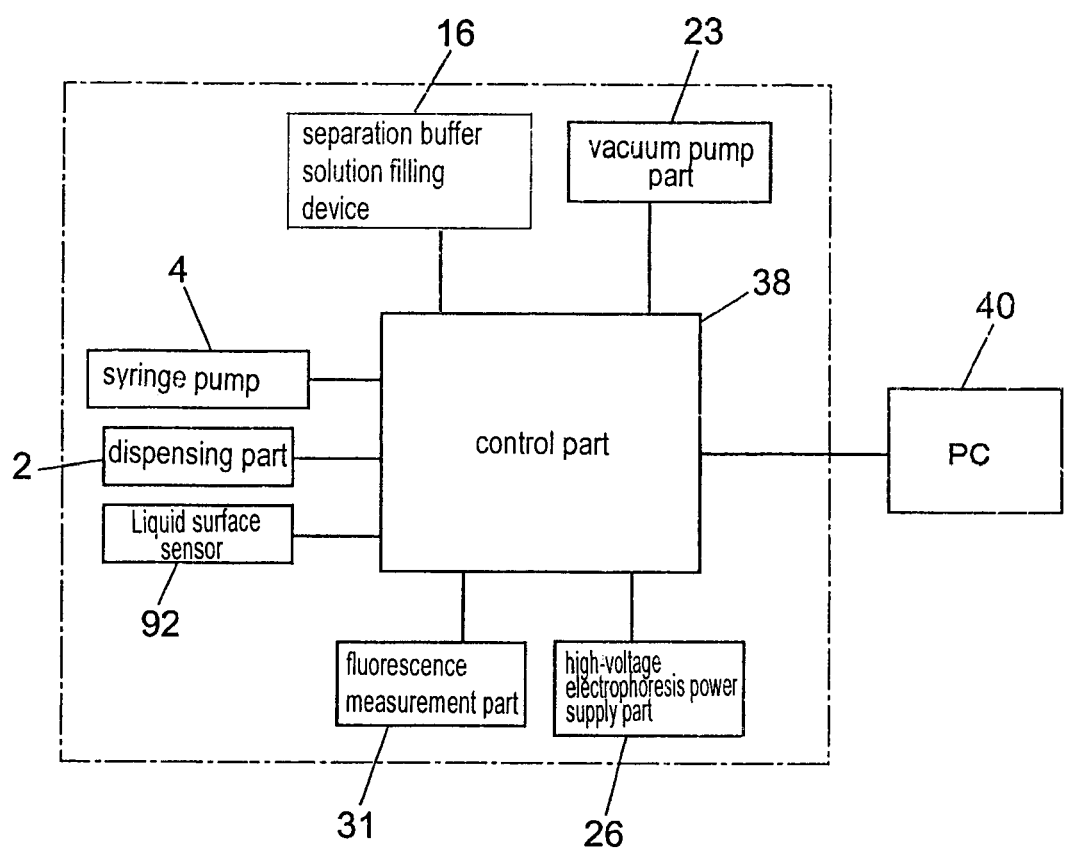
FIG. 1 is a block drawing summarily showing the part related to the control part in one example of a microchip electrophoresis apparatus to which the present invention is applied.

FIG. 1 is a block drawing summarily showing the part related to the control part in one example in which the present invention is applied to a microchip electrophoresis apparatus.

2 is a dispensing part, which includes a dispensing probe driving mechanism having a dispensing probe. The dispensing probe of the dispensing part 2 imbibes a separation buffer solution or a sample by a syringe pump 4 and injects it to one end of the electrophoresis channel of the microchip, and it is provided commonly for plural electrophoresis channels. 16 is a separation buffer solution filling device in which separation buffer solution injected into one end of the electrophoresis channel is filled by air pressure into the electrophoresis channel and superfluous separation buffer solution is discharged by a vacuum pump part 23, and the separation buffer solution filling device 16 also is provided commonly for the plural electrophoresis channels to perform processing. 26 is a high-voltage electrophoresis power supply part which applies phoresis voltage independently to the respective electrophoresis channels. 31 is a fluorescence measurement part as one example of a detection part which detects sample components separated in the electrophoresis channels. 38 is a control part, and it controls the operation of the dispensing part 2 so as to move to separation buffer solution filling and sample injection into the next electrophoresis channel when separation buffer solution filling and sample injection into one electrophoresis channel is finished, and controls the operation of the high-voltage electrophoresis power supply part 26 so as to apply phoresis voltage to cause electrophoresis in the electrophoresis channel in which sample injection was finished, and controls the operation of detection by the fluorescence measurement part 31. 40 is a personal computer as an external control device for instructing the operations of this microchip electrophoresis apparatus and taking in and processing data obtained by the fluorescence measurement part 31.

Figure 2:
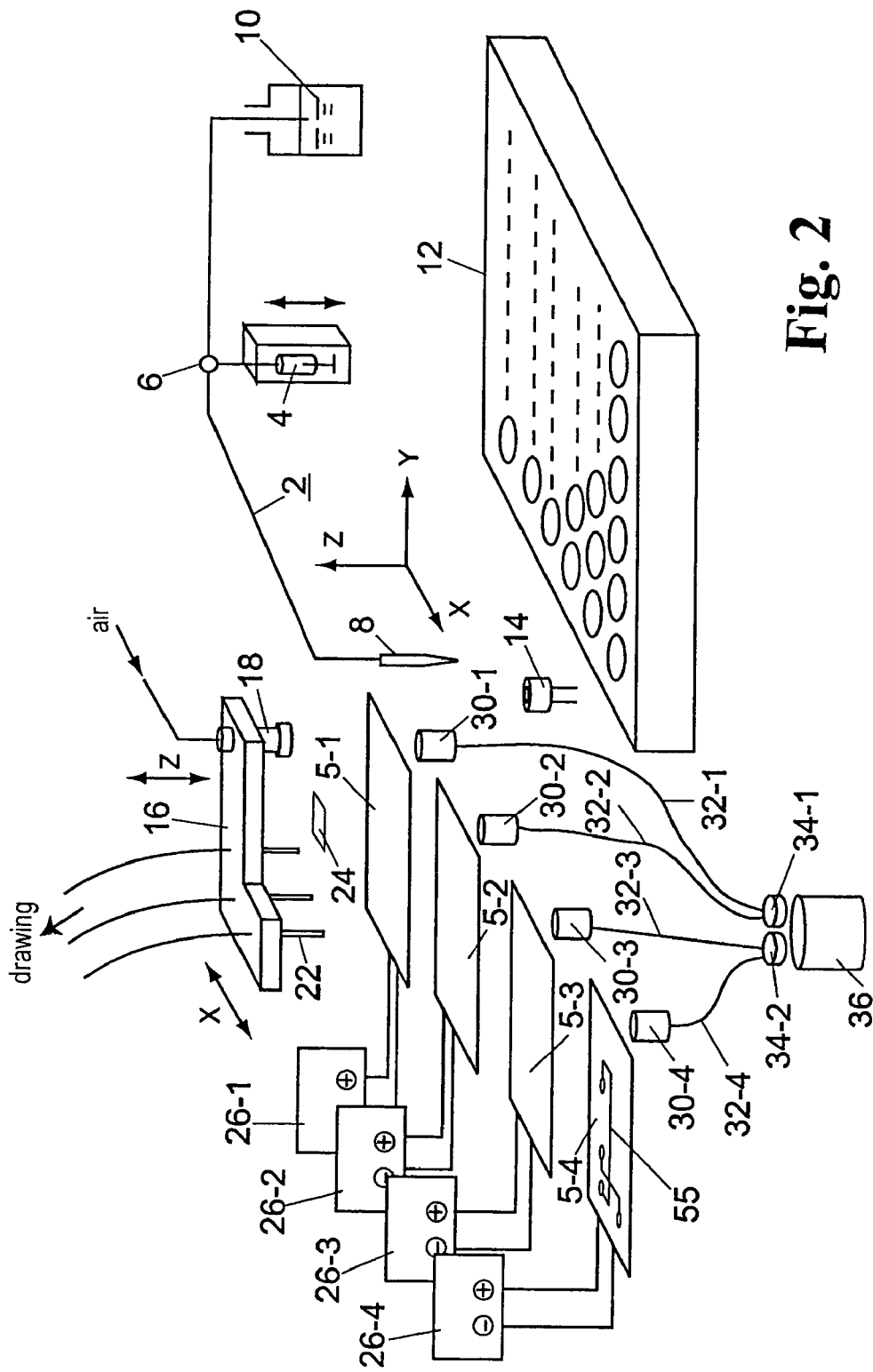
FIG. 2 is a perspective view summarily showing the essential parts of the same microchip electrophoresis apparatus.

FIG. 2 summarily shows the essential parts of a microchip electrophoresis apparatus in one working example. Four microchips 5-1~5-4 are held by a holding part (not illustrated). The microchips 5-1~5-4, as explained in detail later, each have formed one electrophoresis channel for processing one sample In order to dispense separation buffer solution and samples to those microchips 5-1~5-4, the dispensing part 2 has a syringe pump 4 for performing suction and ejection, a dispensing probe 8 having a dispensing nozzle, and a wash solution container 10, and the dispensing probe 8 and the wash solution container 10 are connected to the syringe pump 4 by means of a three-way electromagnetic valve 6. The separation buffer solution and samples are respectively received in holes on a micro titer plate 12, and they are dispensed to the microchips 5-1~5-4 by the dispensing part 2. The separation buffer solution also may be contained in a dedicated container and placed near the micro titer plate 12. 14 is a washing part for washing the dispensing probe 8, and it is overflowing with wash solution.

The dispensing part 2 draws separation buffer solution or sample into the dispensing probe 8 with the three-way electromagnetic valve 6 connected in the direction where the dispensing probe 8 and the syringe pump 4 are connected, and ejects it by the syringe pump 4 into any electrophoresis channel of the microchips 5-1~5-4. When washing the dispensing probe 8, washing is performed by switching the three-way electromagnetic valve 6 to the direction for connecting the syringe pump 4 and the wash solution container 10, and drawing the wash solution into the syringe pump 4, then flooding the dispensing probe 8 with wash solution of the washing part 14, switching the three-way electromagnetic valve 6 to the side connecting the syringe pump 4 and the dispensing probe 8, and ejecting the wash solution from inside of the dispensing probe 8.

The separation buffer solution filling device 16 is provided commonly for the four microchips 5-1~5-4, in order to fill into the channels the separation buffer solution dispensed into the reservoirs on one end of the electrophoresis channels of the microchips 5-1~5-4. The separation buffer solution filling device 16 pushes an air supply port 18 against the reservoir on one end of any electrophoresis channel of the microchips 5-1~5-4 maintaining air-tightness, and inserts suction nozzles 22 into the other reservoirs, and blows air from the air supply port 18 to push the separation buffer solution into the electrophoresis channel, and also draws the separation buffer solution overflowing from the other reservoirs by the vacuum pump from the nozzles 22 to discharge it to the outside.

A high-voltage electrophoresis power supply 26 (26-1~26-4) independent for each microchip 5-1~5-4 is provided in order to apply phoresis voltage independently to the electrophoresis channel of each microchip 5-1~5-4.

The fluorescence measurement part 31 for detecting the sample component electrophoretically separated in the separation channel 55 of the microchip 5-1~5-4 comprises: LEDs (light-emitting diodes) 30-1~30-4 which are provided for each microchip 5-1~5-4 and radiate excited light on a part of the respective electrophoresis channels; optical fibers 32-1~32-4 which receive fluorescent light generated by excitation of sample components moving in the electrophoresis channels by excited light from the LEDs 30-1~30-4; and a photoelectric amplification tube 36 which receives the fluorescent light by means of a filter 34 which removes the excited light component from the fluorescent light from those optical fibers 32-1~32-4 and allows only the fluorescent light portion to pass. By causing the LEDs 30-1~30-4 to emit light with the times mutually shifted, it is possible to identify and detect the fluorescent light from four microchips 5-1~5-4 with one photoelectric amplification tube 36. The light source of the excited light is not limited to LEDs, and LDs (laser diodes) also may be used.

FIG. 3(A)-3(C) and FIG. 4 show one example of the microchip in this working example. The microchip in the present invention indicates such an electrophoresis apparatus having an electrophoresis channel formed inside the substrate, and does not necessarily imply being limited to one having a small size.

Figure 3A:
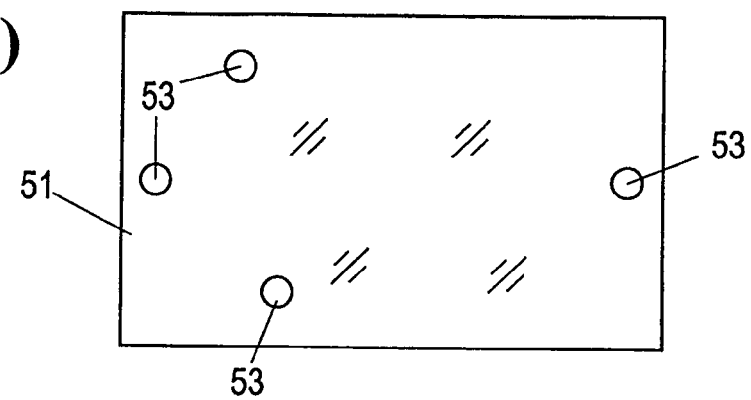
FIG. 3(A)-FIG. 3(C) are drawings showing one example of a microchip.
Figure 3B:
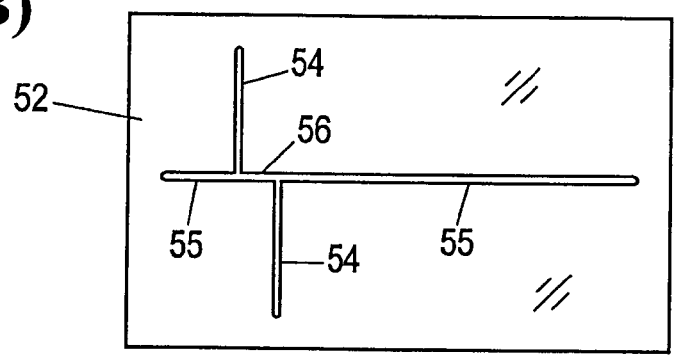
Figure 3C:
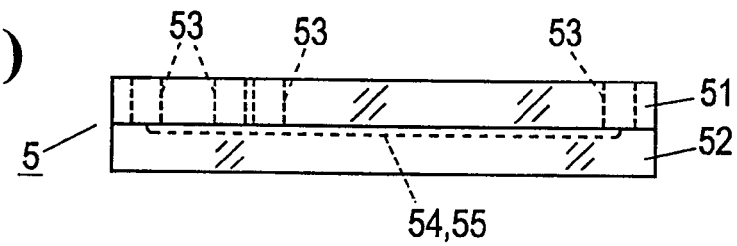

As shown in FIG. 3(A)-3(C), this microchip 5 consists of a pair of transparent substrates (quartz glass or other glass substrates or resin substrates) 51 and 52, and on the surface of one substrate 52, as shown in FIG. 3(B), mutually intersecting capillary electrophoresis grooves 54 and 55 are formed, and on the other substrate 51, as shown in FIG. 3(C), reservoirs 53 are provided as through-holes in positions corresponding to the ends of those grooves 54 and 55. The two substrates 51 and 52 are overlaid and bonded together as shown in FIG. 3(C), and the capillary grooves 54 and 55 are used as a separation channel 55 for electrophoretic separation of samples and a sample introduction channel 54 for introducing samples into that separation channel.

Figure 4:
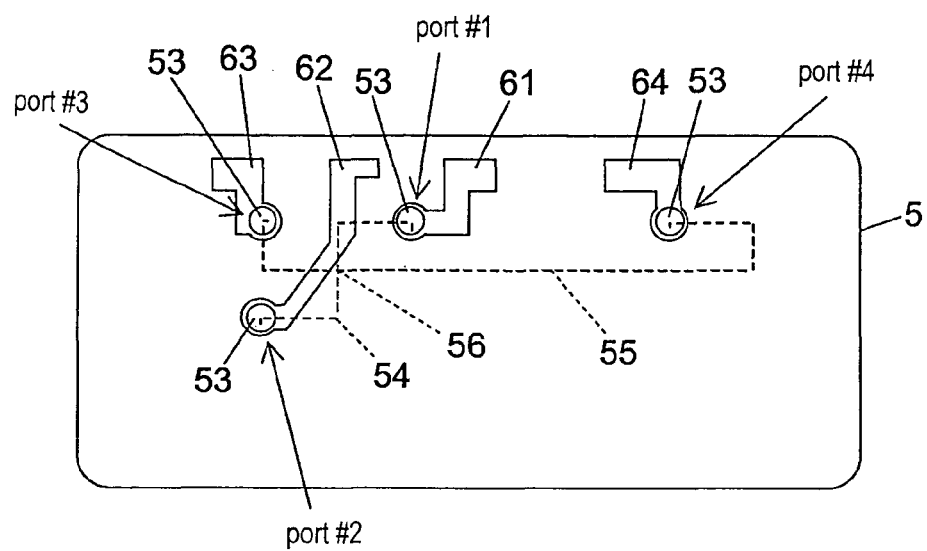
FIG. 4 is a plan view showing a concrete example of a microchip.

The microchip 5 is basically that which is shown in FIG. 3(A)-3(C), but in order to make handling easier, as shown in FIG. 4, one having electrode terminals for applying a voltage formed in advance on the chip is used. FIG. 4 shows a plan view of this microchip 5. The four reservoirs 53 are also ports for applying a voltage to the channels 54 and 55. Ports #1 and #2 are ports positioned on both ends of the sample introduction channel 54, and ports #3 and #4 are ports positioned on both ends of the separation channel 55. In order to apply a voltage to each port, electrode patterns 61~64 formed on the surface of this chip 5 are formed extending from the respective ports to the side end parts of the microchip 5, and they are formed so as to be connected to the high-voltage electrophoresis power supply parts 26-1~26-4.

Figure 5:
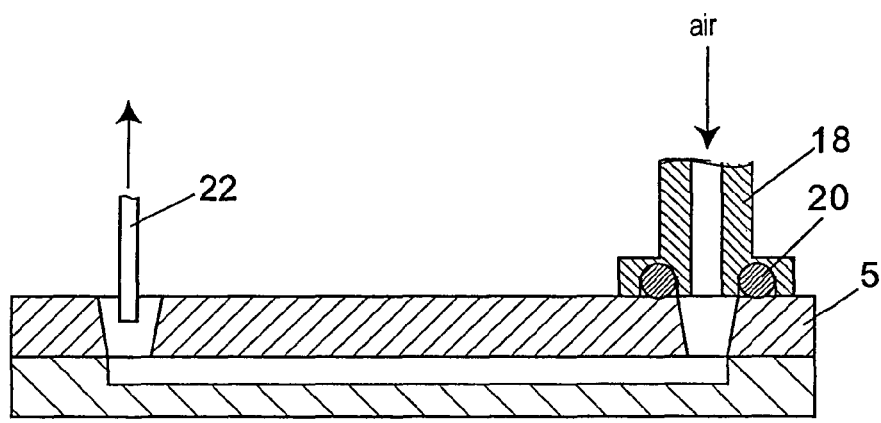
FIG. 5 is a sectional view summarily showing the state of connection between the air supply port and the microchip when filling separation buffer solution in the same microchip electrophoresis apparatus.

FIG. 5 summarily shows the state of connection between the air supply port 18 on the buffer filling/discharging part 16 and the microchip 5. An O-ring 20 is provided on the front end of the air supply port 18, and by pushing the air supply port 18 onto one reservoir of the microchip 5, the air supply port 18 can be attached to the electrophoresis channel of the microchip 5 maintaining air-tightness, and air can be pressurized and sent into the channel from the air supply port 18. The nozzles 22 are connected to the other reservoirs, and the superfluous separation buffer solution overflowing from the channels is imbibed and discharged.

Figure 6B:
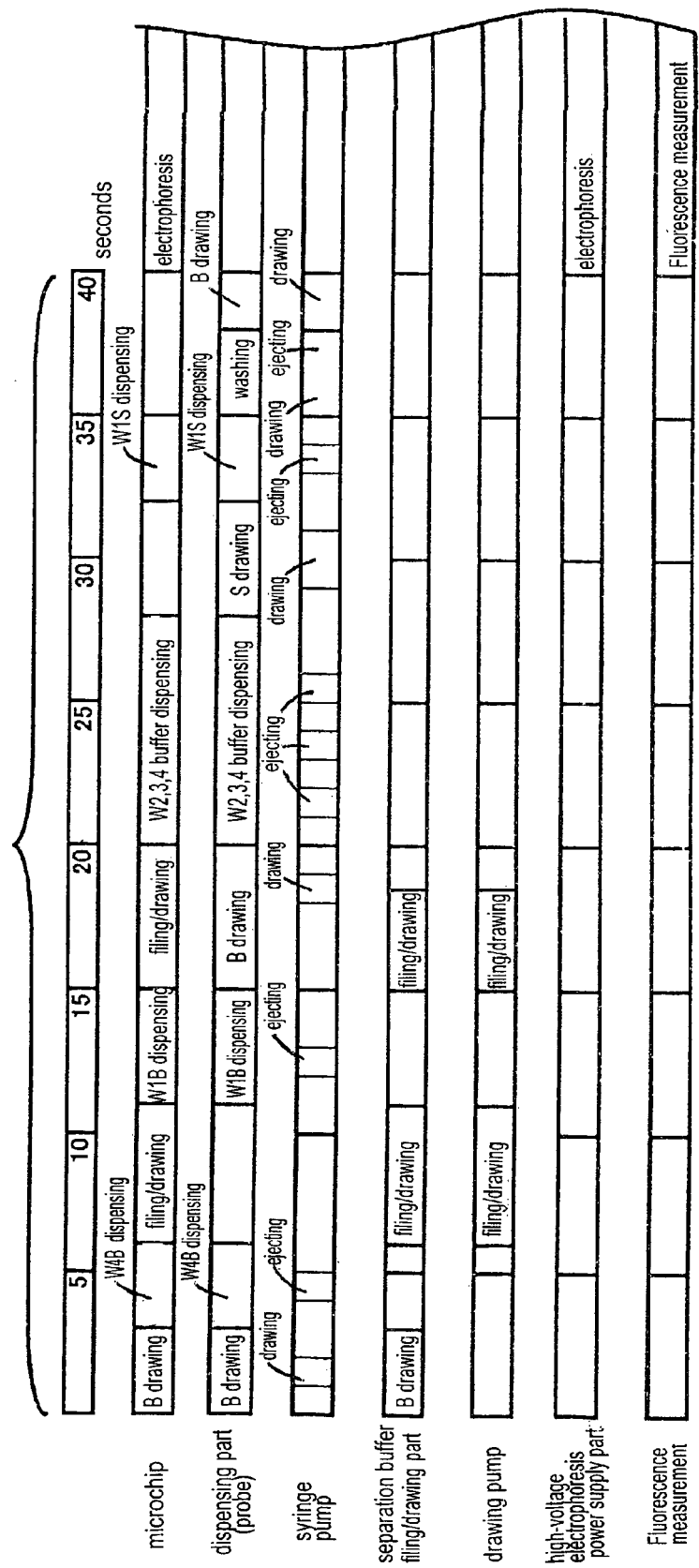

FIG. 6(A)-FIG. 6(B) show in detail the operations in one working example. Here, that which has one electrophoresis channel formed on one microchip is used. Accordingly, in this case, moving of processing from one microchip to the next microchip is the same meaning as moving of processing from one electrophoresis channel to the next electrophoresis channel.

FIG. 6(A) shows the operation of the working example in which a preprocessing process and the electrophoresis/light-measurement process are performed sequentially while partially in parallel on four microchips.

Each process is set in time, the preprocessing process is set to 40 seconds and the electrophoresis/light-measurement process to 120 seconds, and one cycle for one microchip is 160 seconds.

When the preprocessing process for one microchip is finished, it moves to the preprocessing process of the next microchip without waiting for the end of the electrophoresis/light measurement process on the former microchip. That is, electrophoresis is started accompanying the end of the preprocessing process on the first microchip, and light measurement also is started, and in addition, the preprocessing process on the second microchip is started. When the preprocessing process on the second microchip is finished, electrophoresis on the second microchip is started, and light measurement also is started, and in addition, the preprocessing process on the third microchip is started. Thus, the preprocessing process goes on to be performed sequentially for each microchip, and separately from that, on a microchip having finished the preprocessing process, electrophoresis and light measurement go on to be started sequentially, and as a result electrophoresis and light measurement are performed in parallel on plural microchips. When the preprocessing process is performed up to the fourth microchip, because the analysis is finished on the first microchip, the first microchip is reused and the same kind of processing goes on to be repeated.

In the electrophoresis process, application of a voltage in order to lead the sample from the sample introduction channel to the position of intersection with the separation channel is performed, and the next electrophoretic separation by application of a voltage in the separation channel is performed. Along with this, light radiation from the LED is performed in the detection position, and fluorescence measurement is started.

The preprocessing process is shown in detail in FIG. 6(B).

The uppermost numbers represent the time (seconds). The "microchip" fields indicate the contents of the processing in one microchip. The "dispensing part" fields indicate the operations of drawing and ejecting of separation buffer solution and sample from the dispensing probe 8 performed by the syringe pump 4.

The "separation buffer solution filling device" fields indicate the filling operation of pushing the separation buffer solution dispensed to the microchip into the channel and the operation of performing the drawing process of drawing and discharging the overflowing separation buffer solution by the suction pump.

In the "microchip" fields, the first separation buffer solution drawing (B drawing) is the process of drawing and discharging the separation buffer solution used in the first analysis. In the next "W4B dispensing" operation, the separation buffer solution is dispensed to the fourth reservoir, and in the next "filling/drawing" process, pressurized air is supplied from the separation buffer solution filling device and that separation buffer solution is pushed into the electrophoresis channel, and also the superfluous separation buffer solution is drawn in and discharged from the other reservoirs whereby the channels are washed with new separation buffer solution.

By the next "W1B dispensing" process, new separation buffer solution is dispensed into the first reservoir in order to wash the first reservoir, and in the next "filling/drawing" process, pressurized air is supplied to the fourth reservoir from the separation buffer solution filling device and that separation buffer solution is pushed into the electrophoresis channel, and also the superfluous separation buffer solution is drawn in and discharged from the other reservoirs whereby the separation buffer solution is filled into the channels. After that, by the next "W2, 3, 4 buffer dispensing" processes, the separation buffer solution is dispensed also from the other second, third, and fourth reservoirs. With this, filling of separation buffer solution into the electrophoresis channel is completed.

Next, the sample is drawn into the dispensing probe of the dispensing part for dispensing of the sample, and by the "W1S dispensing" process, sample dispensing is performed by ejection of that sample in the first reservoir. After sample dispensing, the dispensing probe of the dispensing part is washed, and then it prepares for imbibing the separation buffer solution for the next sample. With this, the preprocessing process in the electrophoresis channel of that microchip is finished.

In the microchip of the working example, an electrophoresis channel by cross injection method is used, but it is not limited to this, and it also may be a microchip with only a separation channel.

Also, in the microchip of the working example, that which has only one electrophoresis channel on one microchip is used, it also may have plural electrophoresis channels formed on one microchip, and in that case, the present invention should be applied with the electrophoresis channels as a unit.

That which measures fluorescence was used as a detection part, but in addition to measuring fluorescence, it is possible also to measure light absorption or use a detection method using chemical light emission or biological light emission. Regarding the detection part, even if it is not one which radiates excited light independently for each microchip, it also may be a method in which a light measurement system used commonly by all microchips is prepared, and that optical system scans in a manner so as to be moved among the detection positions of all of the microchips.

Next the dispensing part 2 is explained in detail.

Figure 7:
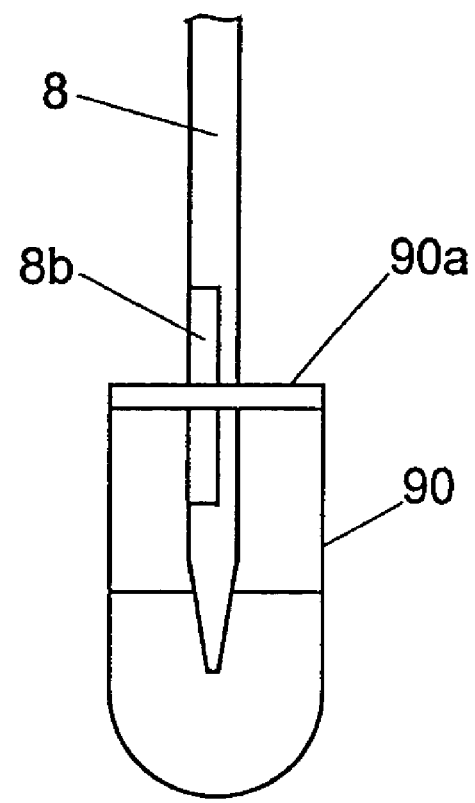
FIG. 7 is a generalized front view showing the dispensing probe in one working example.

As shown in enlargement in FIG. 7, the dispensing probe 8 is hollow and the tip is needle-like, and imbibing and ejecting of liquid are performed from a hole on the tip. The dispensing probe 8 is used commonly by samples and reagents (in this working example separation buffer solution). FIG. 7 shows the state in which the tip of the dispensing probe 8 was inserted into the sample container 90. The sample container 90, as shown in FIG. 7, is installed in this microchip processing apparatus in a state having the upper opening closed by a seal material 90a such as a septum that can be penetrated by the needle of the dispensing probe 8. On the other hand, the reagent container containing the separation buffer solution is installed in this microchip processing apparatus in a state having the upper opening opened by removal of the outer lid. During the sample dispensing operation, the needle of the dispensing probe 8 is inserted into the sample container 90 penetrating the seal material 90a and imbibing of the sample is performed, and during reagent dispensing, the needle of the dispensing probe 8 is inserted into the opened reagent container and imbibing of the reagent is performed.

The dispensing probe 8 has a groove 8b on its side surface. That groove 8b for example has both a width and a height of 50 μm~0.6 mm, and its position is the position where the inside of the sample container 90 and the atmosphere communicate when the tip of the dispensing probe 8 is inserted into the sample container 90 to imbibe the sample, that is, the position where it is penetrating the seal material 90a. By this, because the atmosphere flows into the container 90 through the groove 8b even when the sample inside the container 90 is imbibed by the dispensing probe 8, it is possible to prevent the inside of the container 90 from being negatively pressurized, and the liquid can be drawn with good precision.

The dispensing probe 8 is made of metal, and it serves as an electrostatic capacitance type liquid surface sensor by detection of the electrostatic capacitance at its tip part. The electrostatic capacitance detects the liquid surface by changing when the tip part of the dispensing probe 8 is inserted into the sample container or the reagent container and contacts with the liquid inside the container. The liquid surface sensor, as indicated by symbol 92 in FIG. 1, is connected to the control part 38, and by regularly monitoring the electrostatic capacitance, the position of the liquid surface inside the sample container or the reagent container is sensed.

The control part 38 calculates the remaining liquid quantity inside the sample container or inside the reagent container based on the output of this liquid surface sensor, and performs a display as shown in FIG. 8 with the personal computer (PC) 40 as the remaining liquid quantity display part.

It also may be made such that in the event that the remaining liquid quantity based on the output of this liquid surface sensor was insufficient before the start of analysis, the control part 38 makes that known with the personal computer 40 as a warning means.

It also may be made such that in the event that the remaining liquid quantity based on the output of this liquid surface sensor became insufficient, the control part 38 makes that known at that time with the personal computer 40 as a warning means.

FIG. 9(A)-9(C) show an example in which the dispensing probe driving mechanism in the dispensing part 2 has on the lower end a restraining lever 86 as a restraining mechanism having a horizontal restraining member 86b which forces downward so that the sample container 90 does not come up when the dispensing probe 8 is driven in the Z direction (vertical direction) and the dispensing probe 8 is pulled out from the sample container 90.

The restraining lever 86 is attached to be capable of sliding on a probe holder 80 for holding the dispensing probe 8 and moving in the vertical direction, and it has a spring 87 as a forcing means for forcing the restraining lever 86 downward against the probe holder 80, and a stopper 86a for restricting the restraining lever 86b from moving further downward from the stopping position (position in the state in FIG. 9(A)) of the lower end of the dispensing probe 8 against the probe holder 80. The stopper 86a is fixed on the restraining lever 86 above the probe holder 80, and due to contact with the upper surface of the probe holder 80, the restraining lever 86 is prevented from moving further downward. The spring 87 is a tension spring. This spring is hung above the probe holder 80 between the upper end of the restraining lever 86 and the probe holder 80.

The restraining lever 86 and the dispensing probe 8 are driven by a single-axis drive system for moving the probe holder 80 in the vertical direction. Explaining this mechanism in further detail, the driving part 70 for driving the dispensing probe 8 has a fixed shaft 72 which is fixed to a driving mechanism (not illustrated) for moving this driving part 70 in the X direction and Y direction on a horizontal plane. A vertical linear guide 82 is fixed on the fixed shaft 72, and the probe holder 80 is guided by the linear guide 82, and it is supported to be capable of sliding in the vertical direction. A ball screw 76 is fitted on the probe holder 80, and the movement of the probe holder 80 in the vertical direction is driven by rotation of the ball screw 76. Also, a stepping motor as a drive motor 74, is attached on the fixed shaft 72, and the rotating shaft of the drive motor 74 and the ball screw 76 are linked by a timing belt 78, whereby the rotation of the drive motor 74 is transmitted to the ball screw 76.

The operation of imbibing a sample with the dispensing probe 8 by the dispensing part in FIG. 9(A)-9(C) is explained.

(Waiting State)

The position in FIG. 9(A) is the waiting position, and in the waiting position, the probe holder 80 is raised to the uppermost position, and the restraining lever 86 has become in the state most descended against the probe holder 80 with the stopper 86a of the restraining lever 86 in contact with the upper surface of the probe holder 80. In this waiting state, the restraining member 86b at the lower end of the restraining lever 86 has come further downward from the tip of the dispensing probe 8.

(Descent for Sample Imbibing)

FIG. 9(B) shows the state when the dispensing probe 8 descends. The rotation of the drive motor 74 is transmitted to the ball screw 76 by means of the timing belt 78, and the ball screw 76 rotates whereby the probe holder 80 descends. Because the dispensing probe 8 is fixed to the probe holder 80, it descends together with the probe holder 80. Also, because the restraining lever 86 is forced downward against the probe holder 80 by the spring 87, the restraining lever 86 also descends together with the probe holder 80. The descent of the restraining lever 86 stops when the restraining member 86b at the lower end of the restraining lever 86 contacts with the upper surface of the sample container 90.

(Sample Imbibing)

The probe holder 80 continues to descend further from the state in FIG. 9(B). The restraining lever 86 cannot descend further because the restraining member 86b on its lower end is in contact with the sample container, and the restraining lever 86 slides against the probe holder 80 accompanying descent of the probe holder 80, and only the probe holder 80 continues to descend and the spring 87 goes on to stretch. The dispensing probe 8 descends together with the probe holder 80, and its tip is inserted into the sample container 90 penetrating the shield material 90a of the sample container 90. Because the tip of the dispensing probe 8 serves as a liquid surface sensor, when the liquid surface sensor senses the liquid surface inside the sample container 90, by that, the driving of the drive motor 74 is stopped at the place where it has intruded into the sample by a prescribed depth, and the descent of the probe holder 80 is stopped. That state is the state shown in FIG. 9(C), and in that state a prescribed quantity of sample is imbibed by the dispensing probe 8.

Next, the drive motor 74 rotates in the reverse direction, and the probe holder 80 starts to ascend. The dispensing probe 8 starts to ascend accompanying the ascent of the probe holder 80, and it is pulled out from the sample container 90. At this time, because the restraining lever 86 is being forced downward against the probe holder 80 by the spring 87, the restraining lever 86 stops at the position in FIG. 9(C) even though the probe holder 80 is starting to ascend. By this, although a force in the direction of pulling upward works on the sample container 90 by friction between the dispensing probe 8 and the seal material 90a when the dispensing probe 8 is pulled out from the seal material 90a of the sample container 90, the sample container 90 is prevented from coming up because the restraining member 86b is fixed in the position in FIG. 9(C).

Soon, when the probe holder 80 ascends up to the position in FIG. 9(B), the stopper 86a attached to the restraining lever 86 contacts with the upper surface of the probe holder 80, and after that when the probe holder 80 ascends further, the restraining lever 86 ascends together with the probe holder 80. When the probe holder 80 ascends up to the position in FIG. 9(A), the sample imbibing operation is finished.

After that, the entire driving part 70 is moved up to a prescribed position of the microchip, and the dispensing probe 8 is inserted into a prescribed reservoir of the microchip and the sample is injected.

The dispensing probe 8 is used not only for dispensing of samples, but also for dispensing of reagents. Although the reagent in this working example is separation buffer solution, it is the same even in the case when using other reagents. For the reagent container, one that is larger than the sample container is used in order to contain a reagent that is repeatedly dispensed to the microchip, and it is installed in this microchip processing apparatus in a state having the lid on the open part removed. The dispensing probe 8 has been manufactured with a view that it will be inserted into a reagent container with the lid removed. The lid of the reagent container for example is made of metal, or the like, and it is harder compared with the seal material 90a of the sample container 90, and there is a concern that if it is installed in the microchip processing apparatus with the lid of the reagent container attached, the tip of the dispensing probe 8 may be damaged by being pushed against the lid of the reagent container. As a working example for preventing such a situation, FIG. 10(A)-10(C) shows one in which it has a means for sensing that the dispensing probe 8 hit the lid of the reagent container.

When compared with the driving part 70 in FIG. 9(A)-9(C), the driving part 70a shown in FIG. 10(A)-10(C) differs from the one in FIG. 9 in the point that the mechanism for holding the dispensing probe 8 against the probe holder 80 is different, and it is provided with a sensor for sensing that the tip of the dispensing probe 8 hit the lid.

In the driving part 70a in FIG. 10(A)-10(C), the dispensing probe 8 is held to be capable of sliding against the probe holder 80. The probe holder 80 integrally has an L-shaped spring restraining part 80a which extends upward. The dispensing probe 8 is supported to be capable of sliding running through the probe holder 80 and the spring restraining part 80a, and a compression spring 84 is inserted on the lower side of the spring restraining part 80a and forces the dispensing probe 8 downward against the probe holder 80.

In order to detect that the dispensing probe 8 was displaced against the probe holder 80, the dispensing probe 8 is provided with a protruding piece 8a on the side above the probe holder 80. A position sensor 88 such as a photosensor is provided on the probe holder 80 in order to detect that protruding piece 8a. The positions of both the protruding piece 8a and the position sensor 88 are defined such that the position sensor 88 turns on when the dispensing probe 8 is displaced upward against the probe holder 80 by a prescribed amount.

The operation of sensing that the tip of the dispensing probe 8 hit the lid of the reagent container in the working example in FIG. 10(A)-10(C) is explained.

Although the reagent container 91 should be installed in a state having the lid 91a removed, it is supposed that it was installed in this microchip processing apparatus erroneously with the lid 91a attached.

FIG. 10(A) is the waiting state, and from that state as explained with FIG. 9(A), the probe holder 80 descends, and when the restraining member 86b at the lower end of the restraining lever 86 contacts with the upper surface of the reagent container 91 as in FIG. 10(B), the descent of the restraining lever 86 stops, but the probe holder 80 continues to descend further whereby the tip of the dispensing probe 8 contacts with the lid 91a of the reagent container 91.

The probe holder 80 continues to descend further even after that, but because the dispensing probe 8 cannot penetrate the lid 91a, the dispensing probe 8 stops, and the probe holder 80 continues to descend further sliding against the dispensing probe 8. Because the position sensor 88 is fixed on the probe holder 80, it descends along with the probe holder 80, and soon as shown in FIG. 10(C) the position sensor 88 turns on at the place where the position sensor 88 comes up to the protruding piece 8a, and it is sensed that the tip of the dispensing probe 8 contacts a hard object. In this state the descent of the probe holder 80 is stopped, and the dispensing operation is stopped.

Figure 14R:
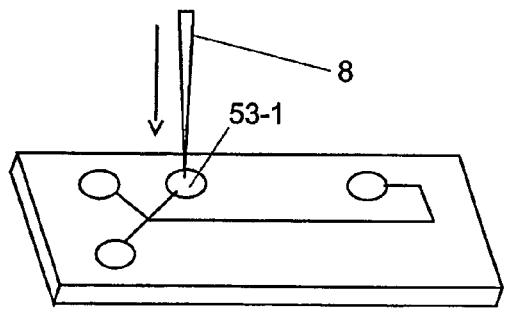
Figure 14S:
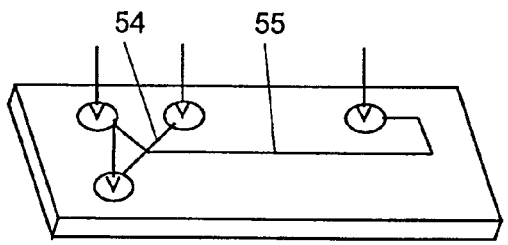
Figure 14T:
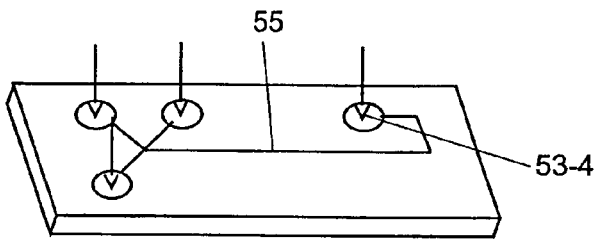
Figure 14U:
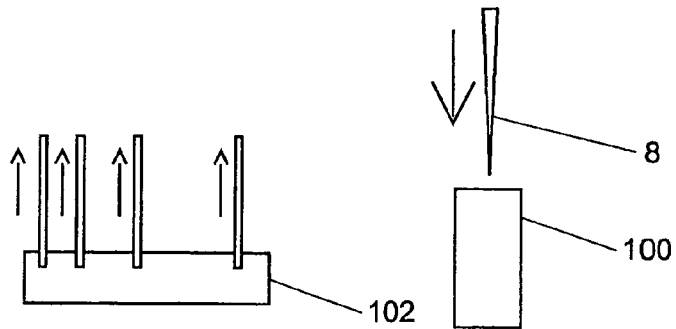
Figure 15:
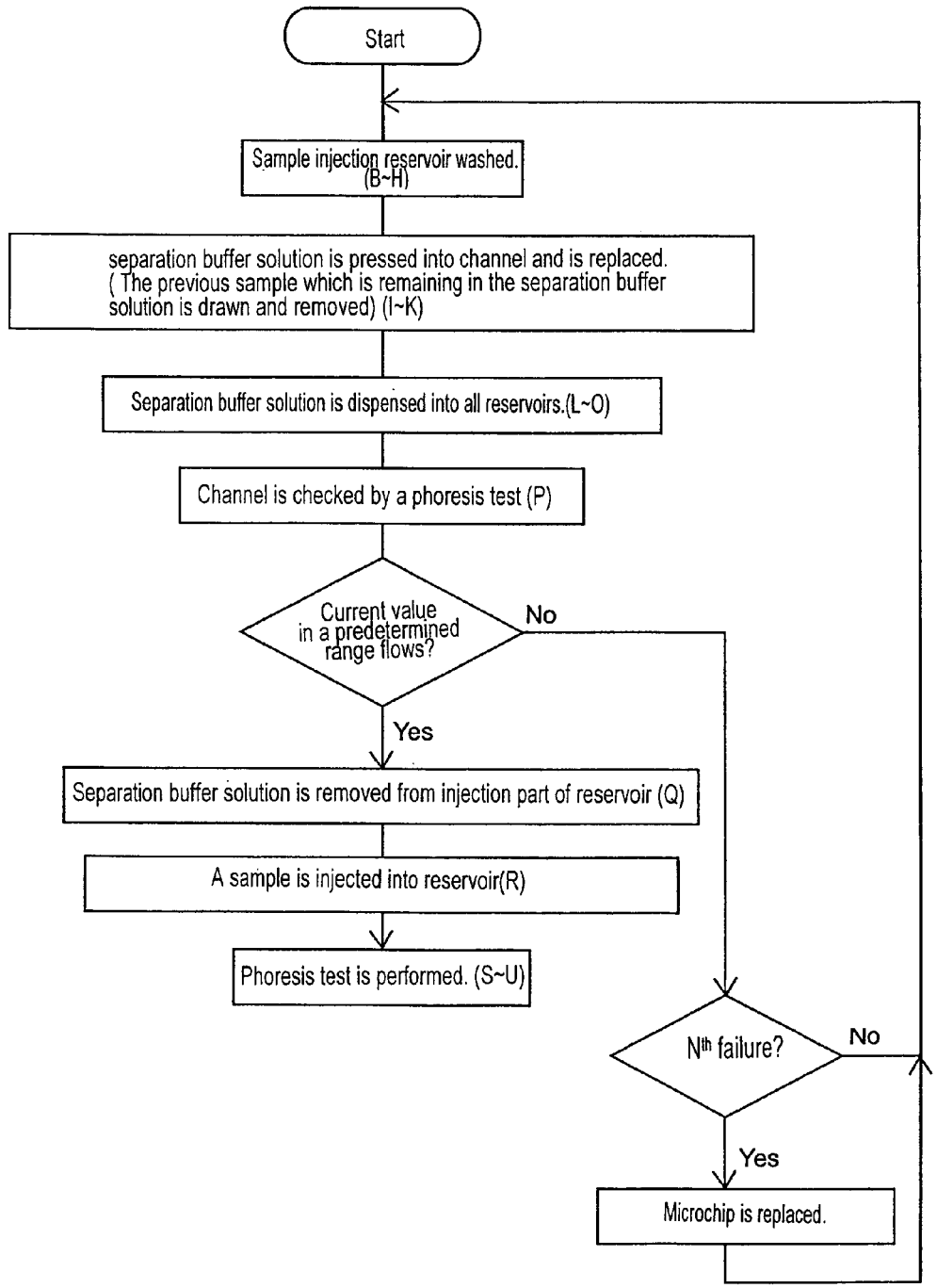
FIG. 15 is a flow chart showing the processing procedure in the operation of the same working example.

The processing procedure in the case when the microchip is repeatedly used in this microchip processing apparatus is shown in FIG. 11(A) to FIG. 14(U), and it is explained using the flow chart in FIG. 15. The symbols (A-U) in the flow chart in FIG. 15 stand for the symbols of the processes in FIG. 11(A)-FIG. 14(U). The processing performed here is a series of processes in which the microchip used in the previous round of analysis is washed, separation buffer solution is filled into the channel, a phoresis test is performed as to whether or not the current flows normally in the channel in a state when separation buffer solution is filled into all reservoirs, and after that a sample is dispensed and phoresis is started, and the dispensing probe and the suction nozzle are washed.

Figure 11A:
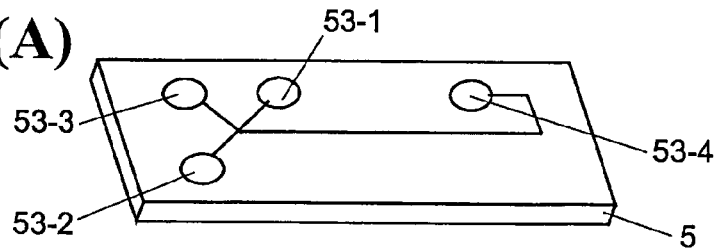
FIG. 11(A)-FIG. 11(E) are perspective views showing the operation of one working example in the order of processes.

FIG. 11(A) shows the microchip 5. The microchip 5 is the one shown in FIG. 3(A) and FIG. 4, it has the separation channel 55 and the sample introduction channel 54 provided in an intersecting manner, and has reservoirs 53 formed on the ends of each channel 54 and 55. The reservoirs from first to fourth in FIG. 4 are indicated here with the symbols 53-1~53-4.

Figure 11B:
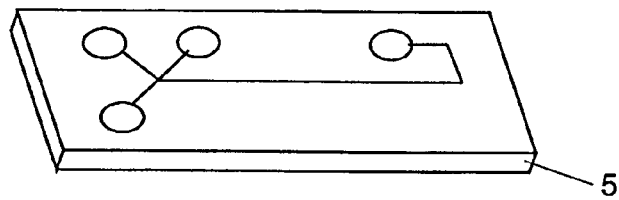

FIG. 11(B) is the state when analysis of the previous sample was finished, and separation buffer solution is remaining in the channels and each reservoir, and separated sample also is remaining in that separation buffer solution.

Figure 11C:
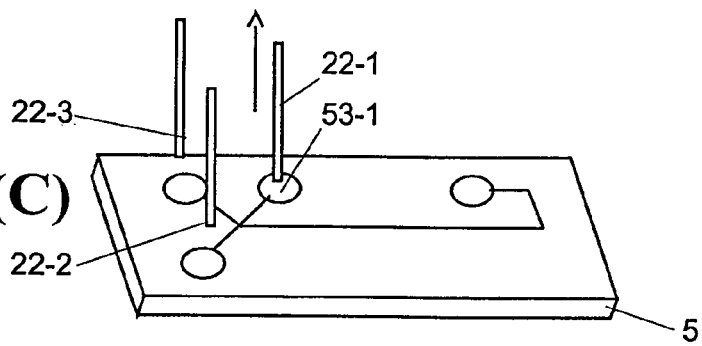

In FIG. 11(C), first, in order to wash the sample injection reservoir 53-1, only the suction nozzle 22-1 is inserted into the reservoir 53-1. The suction nozzle 22-2 and the suction nozzle 22-3 also move vertically simultaneously with the suction nozzle 22-1, but because the length of the suction nozzle 22-1 is longer than that of the other suction nozzles 22-2 and 22-3, only the suction nozzle 22-1 is inserted into the reservoir 53-1 to become in a state being pushed against the bottom part of that reservoir 53-1, but the other suction nozzles 22-2 and 22-3 are not inserted into the respectively corresponding reservoirs 53-2 and 53-3. In that state the separation buffer solution inside the reservoir 53-1 is drawn and removed by being drawn from the suction nozzle 22-1.

Figure 11D:
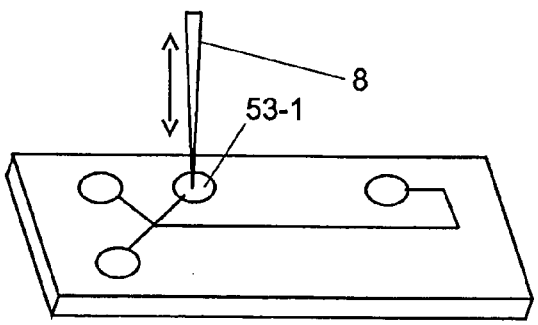

In FIG. 11(D), wash liquid is supplied into the reservoir 53-1 from the dispensing probe 8.

Figure 11E:
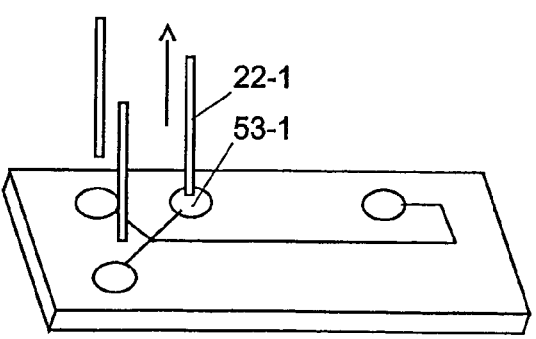

In FIG. 11(E), again the suction nozzle 22-1 is inserted into the reservoir 53-1, and the wash liquid is drawn and discharged.

Figure 12F:
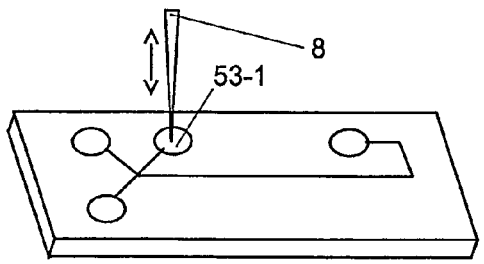

In FIG. 12(F), wash liquid is supplied again into the reservoir 53-1 from the dispensing probe 8.

Figure 12G:
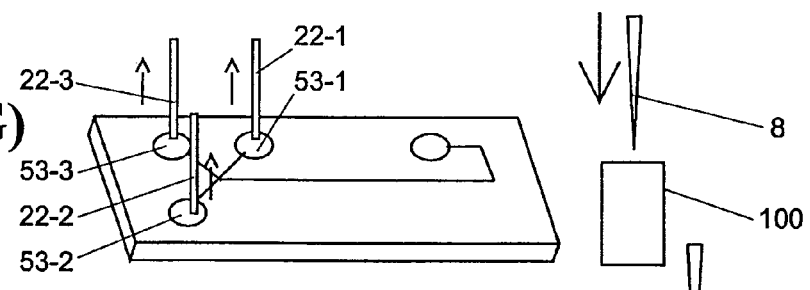

In FIG. 12(G), next, the suction nozzles 22-1~22-3 are inserted respectively into the reservoirs 53-1~53-3. At this time, the three suction nozzles 22-1~22-3 are inserted into the respective reservoirs 53-1~53-3, and they contact with the bottoms of the respective reservoirs by being pushed against them. The liquid is drawn simultaneously by those three suction nozzles 22-1~22-3 and is removed. The dispensing probe 8 is inserted into a rinse port 100 and the entirety of the wash liquid inside the dispensing probe 8 is ejected, and also the inside and outside of the dispensing probe 8 are washed.

Figure 12H:
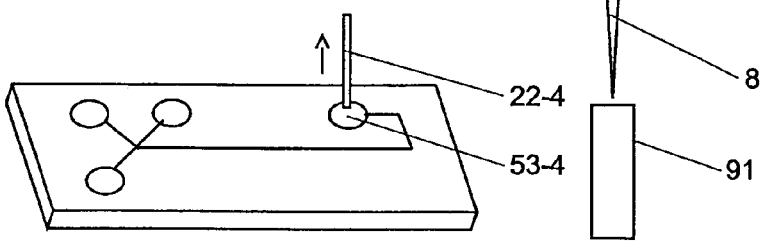

In FIG. 12(H), the fourth suction nozzle 22-4 is inserted into the other one reservoir 53-4. This suction nozzle 22-4 is provided separately from the three suction nozzles 22-1~22-3, and it is placed near a cylinder for air supply port shown in FIG. 15 explained later. The suction nozzle 22-4 also contacts the bottom of the reservoir 53-4 by being pushed against it. The separation buffer solution inside the reservoir 53-4 is drawn by the suction nozzle 22-4 and is removed. The dispensing probe 8 draws the separation buffer solution from the reagent container 91 containing buffer solution.

Figure 12I:
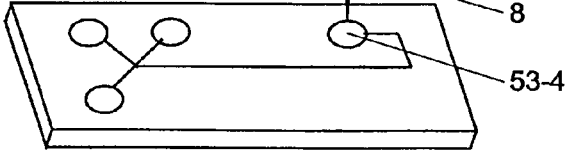

In FIG. 12(I), the dispensing probe 8 is moved to the reservoir 53-4, and it dispenses the separation buffer solution.

Figure 12J:
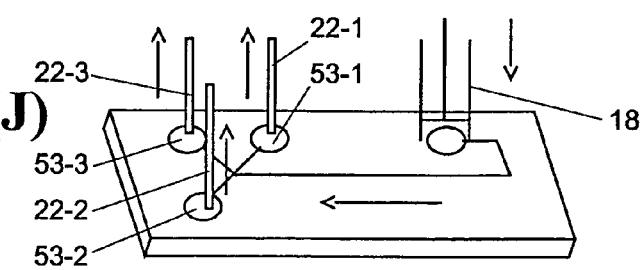

In FIG. 12(J), the air supply port 18 is pushed onto the reservoir 53-4 maintaining air-tightness, and air is supplied into the channel from the reservoir 53-4 by driving of the cylinder shown in FIG. 15 later. The suction nozzles 22-1~22-3 are inserted respectively into the other reservoirs 53-1~53-3, and the separation buffer solution overflowing into the respective reservoirs 53-1~53-3 from the channel is drawn and removed.

Figure 12K:
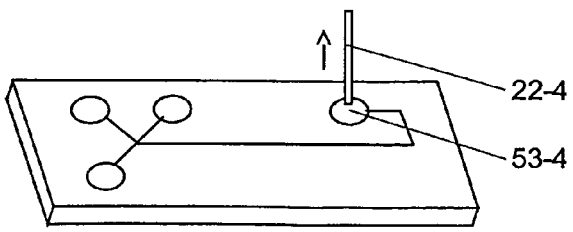

In FIG. 12(K), the suction nozzle 22-4 is inserted into the reservoir 53-4, and the separation buffer solution in that reservoir 53-4 is drawn and removed. By this it assumes a state in which the separation buffer solution remains only in the channel.

In FIG. 13(L)~(O), the separation buffer solution is dispensed sequentially into the reservoirs 53-1~53-4 by the dispensing probe 8.

In FIG. 13(P), electrodes are inserted into the respective reservoirs, and a phoresis test is performed. Here, it is confirmed as to whether or not dirt or bubbles are mixed in the channel by detecting the current value between the electrodes. The voltage applied to the channel here may be the same as the phoresis voltage for separating samples, but it also may be voltage lower than that.

The dispensing probe 8 having dispensed the separation buffer solution is inserted into the rinse port 100, and the separation buffer solution inside the dispensing probe 8 is entirely ejected and also the inside and outside of the dispensing probe 8 are washed.

When it was determined that filling of separation buffer into the channel was performed normally in this phoresis test process, the flow advances to the next process FIG. 13(Q) for injecting the sample and performing analysis, but when it was not determined that filling of separation buffer into the channel was performed normally, the flow returns to the process FIG. 11(B) for refilling of separation buffer solution into the channel.

The number of times (N) that refilling of separation buffer solution into the channel is allowed is set in advance, and when it is not determined that filling of separation buffer solution into the channel was performed normally even when refilling of separation buffer solution was performed that number of times, the flow returns to the process (B) after exchanging with another microchip. The number of times N that refilling of separation buffer solution is allowed is not particularly limited, but for example 2 or 3 is suitable.

In FIG. 13(Q), the suction nozzle 22-1 is inserted only in the sample supply reservoir 53-1, and the separation buffer solution in that reservoir 53-1 is drawn and removed.

In FIG. 14(R), a sample is injected into that reservoir 53-1 from the dispensing probe 8.

In FIG. 14(S), electrodes are inserted into the respective reservoirs 53-1~53-3 and voltage for sample introduction is applied, and the sample is led to the position of intersection of the channels 54 and 55.

In FIG. 14(T), the applied voltage is switched to a voltage for phoresis separation, and the sample is electrophoretically separated toward the reservoir 53-4 in the separation channel 55.

In FIG. 14(U), after the end of analysis, each suction nozzle 22-1~22-4 is inserted into a rinse pool 102 and the wash liquid is drawn, and the insides and outsides of the nozzles are washed, and also the probe 8 is inserted into the rinse port 100 and the inside and outside are washed.

Next, one working example of a separation buffer solution filling device is explained according to FIG. 16(A)-16(C) and FIG. 17.

Figure 17:
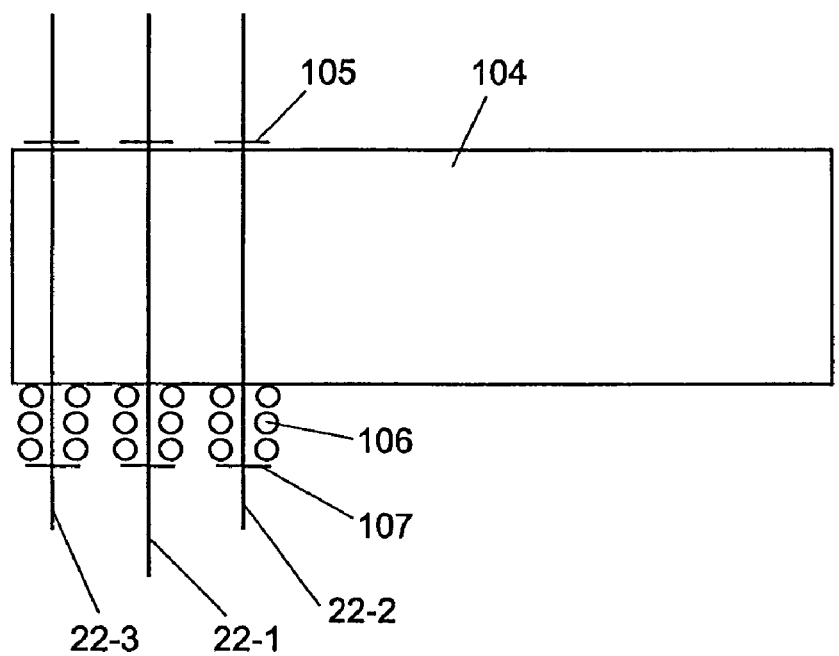
FIG. 17 is a sectional view showing an enlargement of the suction nozzle part in the same separation buffer solution filling device.

The three suction nozzles 22-1~22-3 are held to be capable of sliding on a nozzle holding member 104, and as shown in enlargement in FIG. 17, the range of movement in the vertical direction is restricted by upper and lower stoppers 105 and 107, and they are forced downward from the nozzle holding member 104 by a spring 106. These suction nozzles 22-1~22-3 can be moved upward in opposition to the spring 106 by being pushed against the reservoirs.

As shown in FIG. 16(A), in the state before the suction nozzles are inserted into the reservoirs, the length by which the suction nozzle 22-1 projects downward from the nozzle holding member 104 is set longer than the amount of depth of the liquid present in the reservoir compared with the other suction nozzles 22-2 and 22-3. This means that at the point when the tip of the suction nozzle 22-1 contacts the bottom of the reservoir 53-1 in the state projecting downward, the suction nozzles 22-2 and 22-3 do not yet reach the liquid surfaces inside the reservoirs 53-2 and 53-3. When the needle holding member 104 is moved further downward, all of the suction nozzles 22-1~22-3 contact with the bottoms of the reservoirs.

In this working example, the nozzle holding member 104 doubles as an air cylinder holding member, and a cylinder 108 is fixed to the nozzle holding member 104. A seal part 110 is provided on an open part on the front end of the cylinder 108, and the opening having that seal part serves as the air supply port 18. The cylinder 108 has a plunger 112 on its upper side, and air is ejected from the cylinder by vertical movement of the plunger 112. The plunger 112 is fixed to a plunger holding member 114.

The nozzle holding member (air cylinder holding member) 104 and the plunger holding member 114 are supported to be capable of sliding on a linear guide 116, and a coil spring 118 is inserted between the nozzle holding member 104 and the plunger holding member 114. A stopper 120 which extends upward from the nozzle holding member 104 is provided, and the stopper 120 forms the top dead center of the plunger holding member 114.

This separation buffer solution filling device is fixed to a support body 122, and the support body 122 is attached to a horizontal directional movement mechanism, whereby this separation buffer solution filling device becomes capable of movement in the horizontal direction. As a mechanism for moving the nozzle holding member 104 and the plunger holding member 114 in the vertical direction, a stepping motor is attached as a drive motor 124 to the support body 122, and a ball screw 126 is fitted on the plunger holding member 114. A timing belt 128 is hung between the motor 124 and the ball screw 126, and the rotation of the motor 124 is transmitted to the ball screw 126 by means of the timing belt 128. The plunger holding member 114 is moved in the vertical direction by the rotation of the ball screw 126. In this working example, because the nozzle holding member 104 doubles as an air cylinder holding member, the mechanisms for driving of the suction nozzles 22-1~22-3 and moving and driving of the air cylinder 108 can be driven by one drive motor 124.

In FIG. 16(A)-16(C), an embodiment in which the nozzle holding member 104 does not have suction nozzles 22-1~22-3, that is, an embodiment in which the member 104 functions simply as an air cylinder holding member without performing the function of a nozzle holding member, also becomes one working example of the present invention.

Next, the operation of filling separation buffer solution into the microchip 5 is explained according to FIG. 16(A)-16(C).

This operation corresponds to the processes after the separation buffer solution was supplied to the reservoir 53-4 in FIG. 12(I), and up to when the separation buffer solution is pressed in by supply of air from the air supply port 18 in FIG. 12(J), and also the separation buffer solution overflowing from the channel is drawn by the suction nozzles 22-1~22-3 and discharged.

(A): FIG. 16(A) is the waiting state, and the plunger holding member 114 is at the top dead center. In this state the separation buffer solution has already been supplied to the reservoir 53-4 of the microchip.

(B): The ball screw 126 rotates and the plunger holding member 114 goes down, and the nozzle holding member 104 is pushed down by means of the coil spring 118. As shown in FIG. 16(B), the seal part 110 of the cylinder 108 is made to contact onto the reservoir 53-4 maintaining air-tightness, and simultaneously the three suction nozzles 22-1~22-3 are inserted into the respective reservoirs 53-1~53-3 and become in a state being pushed against the bottoms of the reservoirs.

(C): When the plunger holding member 114 is caused to descend by further rotation of the ball screw 126, further descent of the nozzle holding member 104 is restricted by the lower end of the cylinder 108 contacting with the microchip 5, but as shown in FIG. 16(C), the plunger holding member 114 separates from the stopper 120 by contraction of the coil spring 118 and descends further, and it pushes the plunger 112 to supply air from the air supply port 18. By this, the separation buffer solution inside the reservoir 53-4 is pressed into the channel, and the separation buffer solution overflowing from the channel into the reservoirs 53-1~53-3 is drawn by the respective suction nozzles 22-1~22-3 and is removed.

After the separation buffer solution was pressed into the channel in the state in FIG. 16(C), the ball screw 126 rotates in the reverse direction, and it returns to the state in FIG. 16(B). After that, when the ball screw 126 further rotates in the reverse direction, the plunger holding member 114 hits the stopper 120 whereby the nozzle holding member 104 is pulled up, and it returns to the waiting state in FIG. 16(A).

In the separation buffer solution filling device in FIG. 16(A)-16(C), when the rotation of the ball screw 126 stops at the point when the tip of the suction nozzle 22-1 has contacted the bottom surface of the reservoir 53-1, only the suction nozzle 22-1 is inserted into the reservoir 53-1, and the other suction nozzles 22-2 and 22-3 come to stop at a position not reaching the liquid surfaces of the respective reservoirs 53-2 and 53-3. This state is the state used in FIG. 11(E) and FIG. 13(Q).

Although it is not shown in FIG. 16(A)-16(C), another suction nozzle 22-4 is provided near the cylinder 108, and it is forced downward by a spring just as the other suction nozzles 22-1~22-3. Because the support body 122 is moving in the horizontal direction when that suction nozzle 22-4 is inserted into the reservoir 53-4, the other suction nozzles 22-1~22-3 are not inserted into the respectively corresponding reservoirs 53-1~53-3.

FIG. 18(A)-18(C) show the state of drawing and removal of the liquid inside the reservoir in the case that the suction nozzle 22 (22-1~22-4) contacted a place other than the peripheral part of the bottom surface of the reservoir 53 (53-1~53-3), for example the center part.

The outer diameter of the tip of the suction nozzle 22 is smaller than the size of the bottom of the reservoir 53, and the tip of the suction nozzle 22 is cut diagonally, and it draws liquid from a gap between the bottom surface of the reservoir and the tip of the suction nozzle. When the suction nozzle 22 contacts a place other than the side wall part of the bottom of the reservoir, for example, the center part, the liquid 130 remains in a donut shape at the peripheral part of the bottom of the reservoir. Particularly in the case when this reservoir 53 is a reservoir for sample supply, if it is not cleaned sufficiently, it will become a cause of carry-over to the next analysis. Therefore, in the case when liquid remains at the peripheral part of the bottom of the reservoir, the quantity of liquid for washing the reservoir must be made greater or the number of times of washing must be increased, and the washing time becomes longer, and as a result the overall analysis time becomes longer.

Figure 19:
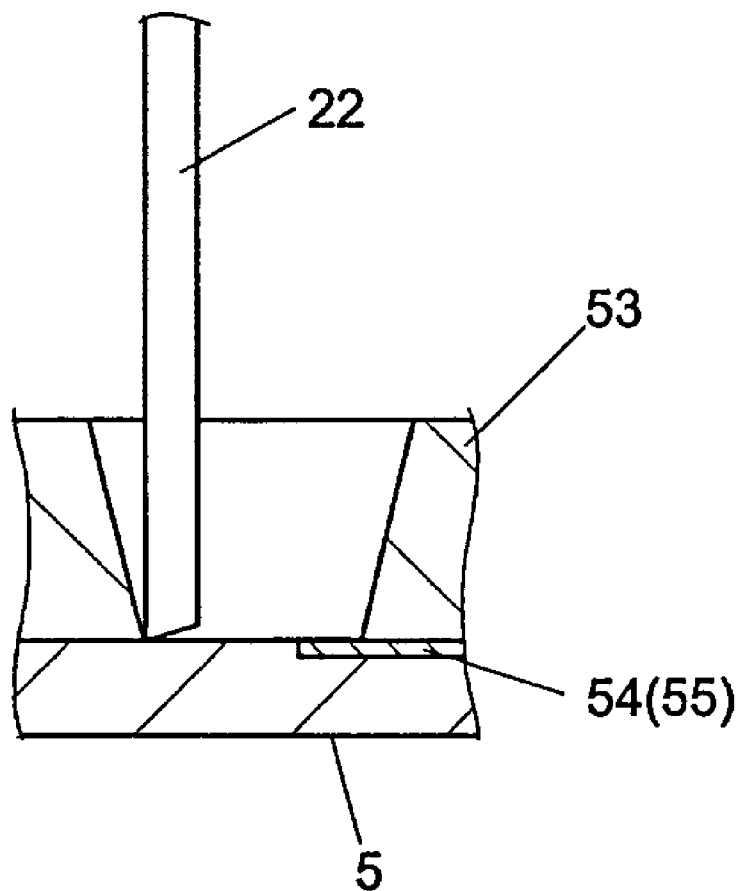
FIG. 19 is a drawing showing an improved method for drawing liquid from the reservoir by the suction nozzle.

Therefore, as a preferred working example, as shown in FIG. 19, the suction nozzle 22 is inserted so as to be pushed against the perimeter wall part of the bottom of the reservoir 53. By adjusting the position of the suction nozzle 22 in this manner, it is possible to draw and remove the liquid without leaving any in the reservoir 53. As a result, the carry-over becomes smaller, and it becomes sufficient with less wash liquid, and the washing time becomes shorter, and as a result the analysis time can be shortened. Also, if under the same washing conditions, the analytical precision is improved by the fact that the carry-over becomes smaller, Reference is made here to matters disclosed in Japanese Patent Application No. 2005-296478, filed on Oct. 11, 2005, and Japanese Patent Application No. 2005-296459, filed on Oct. 11, 2005, and they are to be incorporated into the present application.

Although the present invention was explained up to here based on specific working examples, the above explanation is for the purpose of showing examples, and the present invention is limited only by the claims.

What is claimed is:

1. A separation buffer solution filling device, for a microchip, the microchip having reservoirs opened on a surface, said reservoirs fluidly communicating with channels including at least a main separation channel in which analysis is performed while a solution moves therein, said filling device comprising:

an air supply port is an opening on disposed at a front end of an air cylinder, said air supply port having a seal configured to be pressed against said surface about a selected reservoir to establish an air-tight seal about the selected reservoir;

an air cylinder moving/driving mechanism for moving said air cylinder in a vertical direction with respect to the surface and for operating a plunger disposed in said air cylinder, said air cylinder moving/driving mechanism comprising:

an air cylinder holding member for holding said air cylinder, a plunger holding member for holding said plunger above said air cylinder holding member, a guide for slidably supporting said air cylinder holding member and plunger holding member, an elastic member disposed between said air cylinder holding member and plunger holding member, a driving mechanism for moving said plunger holding member in the vertical direction, and a stopper for defining a top dead center of said plunger holding member; wherein said elastic member is set in a manner such that in a decent of said plunger holding member toward said surface which accompanies an operation of said driving mechanism, said air cylinder holding member is pushed toward said surface by said elastic member until said seal of said air supply port sealingly contacts said surface, and said plunger is pushed further within said air cylinder by the air cylinder moving/driving mechanism to supply air from said air supply port into the selected reservoir.

2. A microchip processing apparatus, comprising at least a holding part for holding a microchip having at least a main separation channel in which analysis is performed while a solution moves inside a plate-like member, a separation buffer solution filling device for filling separation buffer solution into a channel of said microchip, a dispensing probe which is inserted from above into a sample container or a reagent container for imbibing a sample or a reagent and injecting it to a prescribed position on a microchip held on said holding part, and a dispensing probe driving mechanism for moving said dispensing probe between prescribed positions of said microchip, sample container, and reagent container, wherein said separation buffer solution filling device is the device as recited in claim 1.

3. The microchip processing apparatus according to claim 2, wherein: said holding part holds the microchip in a manner such that the number of said main channels becomes plural; a control part is provided in order to control a preprocessing process and an analysis process in said main channels; said dispensing probe is used commonly by said plural main channels, and performs the preprocessing process in advance of the analysis process in those main channels; and said control part controls so that the preprocessing process is performed independently for each main channel such that it moves to the preprocessing process of the next main channel when the preprocessing process in one main channel is finished, and the analysis process is performed in parallel in plural main channels having finished the preprocessing process.

4. A separation buffer solution filling device according to claim 1, further comprising suction nozzles which are inserted into reservoirs other than the selected reservoir and draw the separation buffer solution supplied thereinto from the channels when the separation buffer solution is pushed through the channels by air from said air supply port; and wherein said suction nozzles are slidably supported by a nozzle holding member which moves in the vertical direction, and are forced toward said surface by forcing means, whereby the suction nozzles are pushed against bottoms of the reservoirs into which the suction nozzles are inserted.

5. A separation buffer solution filling device according to claim 4, wherein the suction nozzles are arranged such that a length of a selected suction nozzle projects beyond a remainder of the nozzles so as to be longer by a depth of a liquid present in the reservoirs into which a reminder of the suction nozzles are directed.

6. A separation buffer solution filling device according to claim 4, wherein an outer diameter of a front end of said suction nozzle is smaller than a size of a bottom of said reservoir into which it is inserted, and the front end of the suction nozzle is pushed against a side wall part on the bottom of the reservoir when said suction nozzle imbibes liquid from said reservoir.

7. A separation buffer solution filling device according to claim 4, wherein said air cylinder holding member is integrated with said nozzle holding member.

8. A separation buffer solution filling device according to claim 1, further comprising:
a holding part for holding the microchip;
a dispensing probe which is inserted into a sample container or a reagent container for imbibing a sample or a reagent and injecting it to a prescribed reservoir on the microchip held by said holding part, and
a dispensing probe driving mechanism for moving said dispensing probe between prescribed positions of said microchip, sample container, and reagent container.

9. A separation buffer solution filling device according to claim 1, wherein said elastic member is a spring disposed adjacent the air cylinder.

* * * * *